(12) United States Patent
Cole et al.

(10) Patent No.: US 9,006,660 B2
(45) Date of Patent: Apr. 14, 2015

(54) SCANNING TERAHERTZ PROBE

(75) Inventors: Bryan Edward Cole, Cambridge (GB); Vincent Patrick Wallace, Cambridge (GB); Michael John Withers, Cambridge (GB); John Baker, Cambridge (GB); Brian Robertson, Cambridge (GB)

(73) Assignee: TeraView Limited, Cambridge (GB)

(*) Notice: Subject to any disclaimer, the term of this patent is extended or adjusted under 35 U.S.C. 154(b) by 813 days.

(21) Appl. No.: 12/675,887

(22) PCT Filed: Aug. 28, 2008

(86) PCT No.: PCT/GB2008/002907
§ 371 (c)(1), (2), (4) Date: Oct. 12, 2010

(87) PCT Pub. No.: WO2009/027675
PCT Pub. Date: Mar. 5, 2009

(65) Prior Publication Data
US 2011/0028824 A1    Feb. 3, 2011

(30) Foreign Application Priority Data
Aug. 28, 2007  (GB) .................................. 0716699.4

(51) Int. Cl.
*G01J 5/02*  (2006.01)
*A61B 5/00*  (2006.01)
(Continued)

(52) U.S. Cl.
CPC ............ *A61B 5/0086* (2013.01); *A61B 5/0062* (2013.01); *G01N 21/3581* (2013.01); *A61B 1/00096* (2013.01); *A61B 1/00172* (2013.01); *A61B 5/7257* (2013.01)

(58) Field of Classification Search
CPC ..... G01N 21/3581; G01J 5/02; A61B 5/0062; A61B 1/00096
USPC ........................................................ 250/341.8
See application file for complete search history.

(56) References Cited

U.S. PATENT DOCUMENTS 6,134,003 A * 10/2000 Tearney et al. ............... 356/479
6,706,004 B2 * 3/2004 Tearney et al. ............... 600/587
(Continued)

FOREIGN PATENT DOCUMENTS

GB    2 405 263 A    2/2005
GB    2 411 093 A    8/2005
(Continued)

OTHER PUBLICATIONS

J. J. Pan, "Microwave Optics for Space and Ground Communications," Telesystems Conference, 1993. 'Commercial Applications and Dual-Use Technology,' Conference Proceedings, National Atlanta, GA, USA, Jun. 16-17, 1993.

*Primary Examiner* — Marcus Taningco
(74) *Attorney, Agent, or Firm* — Dickstein Shapiro LLP

(57) ABSTRACT

A THz radiation probe (1) for examining an object (8), the probe comprising a first portion configured to be inserted into an opening of said object in a first direction (5), said probe further comprising at least one THz emitter (15), directing means (7) for directing THz radiation emitted from said emitter to said object via an aperture (2) located at said first portion and subsequently from said object to at least one THz detector (17) and, means for scanning said emitted THz radiation across said object in a scan direction, said scan direction having a component in said first direction (5).

27 Claims, 39 Drawing Sheets

(51) Int. Cl.
*G01N 21/3581* (2014.01)
*A61B 1/00* (2006.01)

(56) References Cited

U.S. PATENT DOCUMENTS 7,242,832 B2 * 7/2007 Carlin et al. .................. 385/116

2003/0004412 A1 * 1/2003 Izatt et al. ..................... 600/425
2005/0100866 A1 * 5/2005 Arnone et al. ................ 433/215

FOREIGN PATENT DOCUMENTS

| JP | 2006-218193 A | 8/2006 |
| WO | WO 02/096479 A2 | 12/2002 |
| WO | WO 2005/019810 A2 | 3/2005 |

* cited by examiner

SCANNING TERAHERTZ PROBE

The present invention relates generally to the field of probes, apparatus and methods for investigating or examining samples. More specifically, the present invention relates to investigation and imaging using a probe that generates and detects Terahertz (THz) radiation. Even more specifically, the present invention relates to the field of investigating human or animal tissue using a probe that uses pulsed THz radiation. The present invention is primarily intended for use in the frequency range 25 GHz to 100 THz, known colloquially as the THz range.

There has recently been much interest in using THz radiation in a wide variety of fields. One such field is medicine, where it has been noted that THz radiation can be used to distinguish between healthy and cancerous tissue. The present invention is by no means limited to the detection of cancerous tissue, or indeed to medical uses in general. However, some of the benefits of the present invention are exemplified here using examples from this field, in particular the breast.

During surgery, for example to remove cancerous tissue, a surgeon must either treat or remove all of the cancerous tissue whilst removing minimal healthy tissue. If, after the surgery, cancerous tissue either remains in the body or remains untreated, then the cancer may return. Conversely if, in an effort to remove or treat all cancerous tissue, too much healthy tissue is removed or treated, then this may adversely affect the patient.

It is difficult to distinguish between cancerous and healthy tissue. A visual examination may not be adequate, since visually the abnormal and normal tissues may be very similar. Further, the margin between cancerous and healthy tissue may be complex, with fine regions of cancerous tissue extending into the healthy tissue.

To aid the differentiation, a biopsy of the tissue is often performed, before, during or after surgery. A biopsy performed during surgery will often be used to determine the nature of the tissue at the margin of an incision, this in turn will give information on whether more tissue should be removed or if sufficient has been taken. However, the results of a biopsy will generally not in be available in real time, since such examinations take several minutes, or even hours, significantly extending the length of the surgery. In situations where the biopsy results are available only after the surgery has been completed, and the results indicate that more tissue should be removed, another surgical procedure will be necessary.

To overcome the lack of a real time analysis of tissue state, during surgery of the breast, for example, the surgeon may use intra-operative palpation and/or specimen radiography of the excised tissue to determine tumour margins. Both of these techniques can sometimes underestimate the extent of the tumour and thus are not particularly reliable consequently, in up to 30% of procedures, cancerous tissue remains in the body.

There is thus a need to be able to distinguish between healthy and abnormal tissue in situ and in real time during surgery so that an informed decision on what tissue to treat or remove can be made.

Distinguishing between cancerous and healthy tissue is further complicated if the incision made in the body is of a nature that impedes the direct visual examination of the area of interest. For example, a surgical incision may take a form that approximates a cylinder. In the specific case of breast surgery this cylinder will often extend from the skin all the way to chest-muscle wall. Such an incision will ensure that no cancerous tissue can remain beyond the base of the cylinder. The nature of the tissue in the lateral wall of the cylinder will then be of most significance in determining whether any cancerous tissue remains within the body. In such a situation, a direct visual examination of the lateral wall of the incision will be difficult since at best, an oblique view of the wall will be available.

However, the present invention may also be used for endoscopic applications or the like where the apparatus is inserted through a surgical opening or a bodily orifice, for example the gastrointestinal tract, cervix or oral cavity.

Previous work has demonstrated that THz radiation may be of use in distinguishing between abnormal and healthy tissue. For example, GB2415777 discloses a THz system that is directed toward the differentiation between normal and cancerous tissues.

Previous THz imaging systems, such as those disclosed in GB2380920 have been of a physical size that precludes their use within the confines of the human or animal body. Typically, in situations where an image of human or animal tissue was required, samples of the tissue were removed from the body for examination. These samples are then generally moved in relation to a static THz imaging system to provide a 2-D or 3-D image. Even with recent advances in the field, THz imaging devices are of a physical size that prevents insertion of the entire device into the body.

Probe devices that emit and/or detect THz radiation have previously been disclosed, for example in GB2371618.

There is therefore a need for a THz probe device that can be partially or fully inserted into the body to detect the presence of abnormal tissue over an extended region. Such a probe can, for example, enable an image of the tissue under examination to be generated using information gained from reflected THz radiation.

Accordingly, in a first aspect the present invention provides a THz radiation probe comprising a portion suitable for insertion into an opening and a portion suitable to be held by hand, the direction between these portions being defined as the probe axis direction, said probe further comprising at least one THz emitter, means for directing THz radiation emitted from said emitter to an aperture located at said portion suitable for insertion and subsequently from said aperture to at least one THz detector and means for scanning said emitted THz radiation across said object wherein; said scanning means is configured to scan said emitted THz radiation in a direction substantially parallel to said probe axis direction.

In a second aspect, the present invention provides a method of analysing an object comprising inserting a first portion of a probe into an opening in a first direction, directing THz radiation emitted from at least one emitter to said object via an aperture in said first portion, directing THz radiation returned from said object to at least one THz detector and, scanning said emitted THz radiation across said object in said first direction.

Embodiments of the invention will now be described, by way of example only, with reference to the following figures in which FIG. 1a shows a cross-sectional view of a probe according to an embodiment of the invention in use.

Figure 1A:
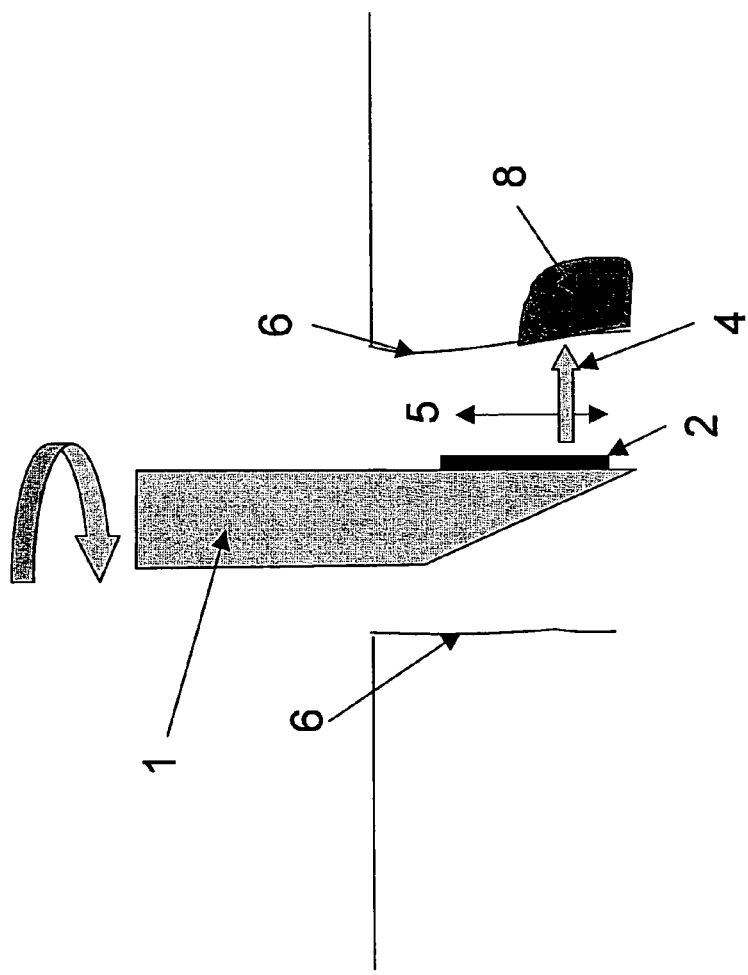
FIG. 1b shows a 3-dimensional schematic view of a probe according to an embodiment of the invention.

FIG. 1a shows a probe 1 according to an embodiment of the invention in use. In FIG. 1a, it is used to examine the inside of an incision made in a human or animal body. Such an incision will often take the form that approximates a cylinder with sides 6 that are approximately perpendicular to the surface in which the incision is made. In use, the end portion of the probe 1 is inserted into the incision, and the geometry of the incision necessitates that the insertion direction 5 is approximately parallel to the sidewalls 6 of the incision. The inserted portion of the probe is held in contact with, or close to, the sidewall 6 of the incision.

The probe 1 is configured such that it emits THz radiation from a region of the inserted portion of the probe 1 that is in contact with the sidewall 6 of the incision. The THz radiation 4 is emitted in a direction that is approximately perpendicular to the insertion direction 5. This emitted radiation will thus be incident on a region of the sidewall 6 of the incision, and will be scanned along the sidewall, as is described in further detail below. Subsequently, some of the incident THz radiation 4 will be reflected by the sidewall 6 back into the probe 1. The probe 1 is configured to detect this reflected radiation and, by measuring certain aspects of the reflected radiation, information about the nature of the sidewall 6 of the incision can be determined.

As an example, in FIG. 1a, a region 8 on the sidewall 6 of the incision is abnormal (for instance cancerous) tissue, whilst the rest of the sidewall 6 is normal tissue. THz radiation reflected from the abnormal tissue region 8 will differ in certain aspects from THz radiation reflected from normal tissue, and from this difference the presence of abnormal tissue can be determined.

The probe 1 is further configured such that the region from which the THz radiation is emitted can be scanned in a direction parallel to the insertion direction 5 of the probe 1. By scanning in this manner, a plurality of measurements can be made in a line along the scan direction. Thus, the extent of any abnormal tissue may be determined in this direction.

Similarly, the probe 1 can be further configured such that it can take measurements from THz radiation that has been reflected from different depths within the sidewall 6, and thus the extent of any abnormal tissue may be also determined in the depth direction. By combining the measurements from different depths and positions along the scan direction, a set of measurements from a two-dimensional slice of the sidewall 6 may be obtained.

In this embodiment, the probe is a hand held probe, and a surgeon can move the probe within the incision to scan the walls of the incision.

Thus, the operator of the probe 1 can rotate the probe 1 about an axis parallel to the insertion direction 5, or alternatively laterally displace the probe 1 in a direction substantially perpendicular to both the insertion direction 5 and the emission direction 4.

By making either of these movements, the two-dimensional slice of the sidewall that is under examination can be changed. By recording data from different slices, a set of data from a three-dimensional region can be obtained.

Information regarding the measurements made by the probe may be presented to the operator in many different forms. One form is an indication, or alarm, that abnormal material has been detected.

A further form is to present a one, two or three-dimensional map of the regions of the material under examination that are considered to be normal or abnormal. Such a map may be presented for example on a screen or in printed form.

Figure 1B:
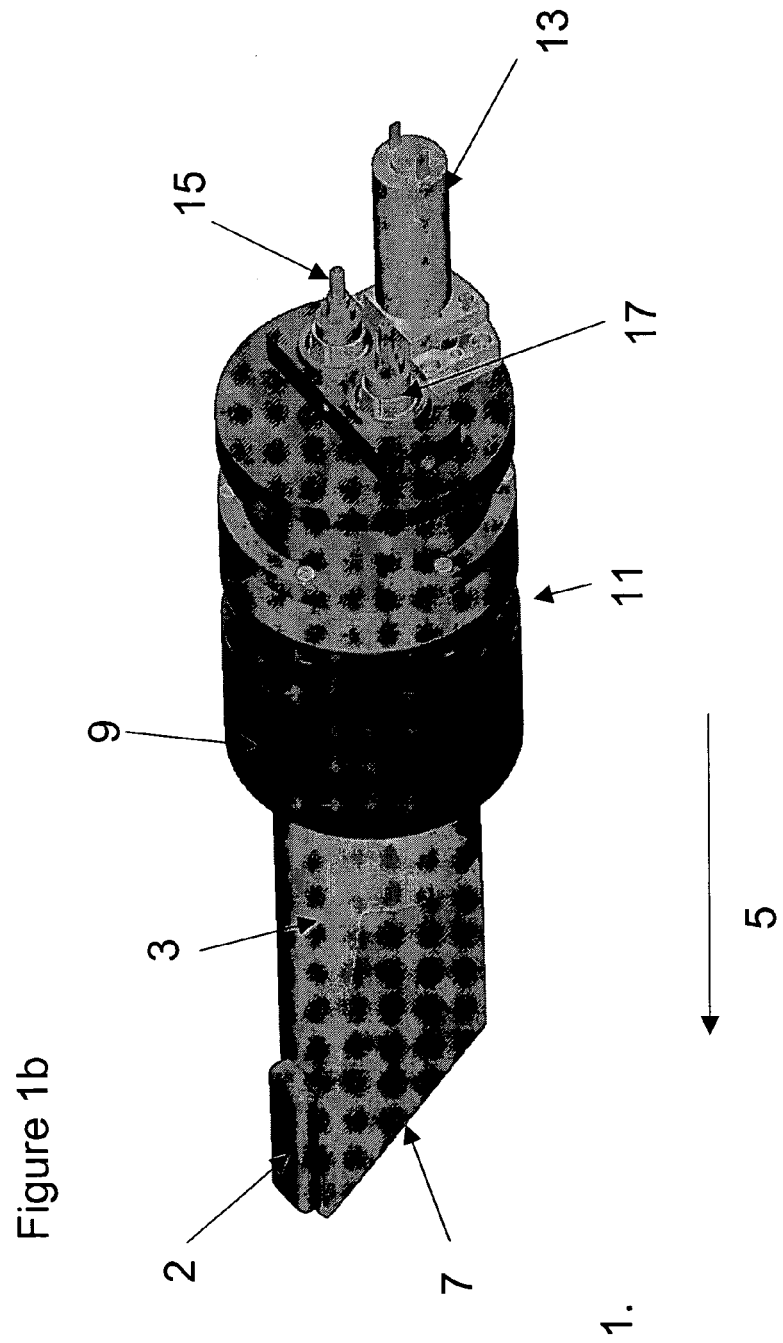

FIG. 1b shows a hand-held THz probe 1 according to an embodiment of the invention. At one end of the probe 1, two cartridges 15, 17 are located side-by-side within the probe 1. One cartridge 15 functions to emit THz radiation for transmission through the probe 1 to a sample, while the other cartridge 17 functions to detect THz radiation reflected from the sample that has propagated back through the probe 1. THz radiation emitted from the emitter cartridge 15 is in the form of a collimated beam, while the receiver cartridge 17 is configured such that it can receive a similarly collimated beam of THz radiation. The construction of the cartridges 15, 17 will be described in greater detail in relation to FIG. 4 below.

On emission from the transmitter cartridge 15, the emitted THz radiation beam is incident on a pair of Risley prisms 11. The Risley prisms 11 are positioned such that the normals to their optical surfaces are substantially parallel to the direction in which THz radiation exits the transmitter cartridge 15. This direction also defines a first probe direction 5. The Risley prisms 11 are mounted such that they can be rotated about an axis that is parallel to this first probe direction 5. An electrical drive system 13 is connected to the Risley prisms 11 to effect the rotation of the prisms 11. The function and effect of the Risley prisms 11 will be described in greater detail in relation to FIGS. 2a and 2b below.

After passing through the Risley prism pair 11, the transmitted THz radiation is incident on a hemispherical lens 9. This lens 9 is fabricated from a material that is transmissive to THz radiation, such as Silicon, and functions to focus the emitted beam of THz radiation from the transmitter cartridge 15.

Abutting the lens 9 is an elongate solid dielectric member 3. The elongate direction of the member 3 is parallel to the first probe direction 5. At the opposite end of the dielectric member 3 to the lens 9 in the first probe direction 5, the dielectric member 3 has a plane surface 7 that is angled at approximately 45° to the first probe direction 5. Thus, the transmitted THz radiation that propagates through the dielectric member 3 will be incident on the plane surface 7 at approximately 45°. In practice, the dielectric member 3 and lens 9 may be formed from one continuous piece of dielectric material.

The refractive index of the dielectric member 3 for THz radiation is such that the THz radiation undergoes total internal reflection at the plane surface 7. The THz radiation is thus deviated through an angle of approximately 90°, and subsequently travels substantially perpendicular to the first probe direction 5. The reflected THz radiation then exits the dielectric member 3 via one of its elongate sides. A window 2 made from a material such as quartz abuts the surface of the dielectric member 3 such that the THz radiation exiting the member passes through the window 2.

The focal length of the lens 9 is chosen to be equal to the optical path length from the principle plane of the lens 9 to the external surface of the quartz window 2, including the reflection from angled surface 7. Thus, the collimated beam of THz radiation from the transmitter 15 is brought to a focus at the quartz window 2.

In use, the probe is placed such that the quartz window 2 is adjacent to a sample to be analysed. THz radiation from the probe 1 that exits the probe via the quartz window 2 will therefore be incident on the sample. The sample will reflect some of the incident THz radiation, and this reflected radiation will re-enter the probe 1. Reflected THz radiation will then propagate through the probe taking a similar path to the transmitted radiation, but in the opposite direction.

After passage through the quartz window 2 and dielectric member 3, reflected THz radiation will again pass through the lens 9. Having been focussed at the quartz window 2, the reflected THz radiation will be divergent when it is incident on the lens 9. Thus the lens 9 will tend to collimate the reflected radiation into a beam, this collimated beam will subsequently enter the receiver cartridge 17 for detection and analysis.

The quartz window 2 will tend to transmit most of the THz radiation, however it will also reflect a portion of the incident THz radiation. The reflected radiation can be used as a reference signal to aid in the calibration of data. This method of using a reflection from quartz is disclosed in GB2415777.

The THz probe 1 is encased in a sterile sheath (not shown), which is made from a thin material, such as plastic, that is substantially transparent to terahertz radiation. The sheath is removable, and can be removed and exchanged for a sterile replacement between patients, allowing sterile medical use of the probe 1.

Figures 2A, 2B:
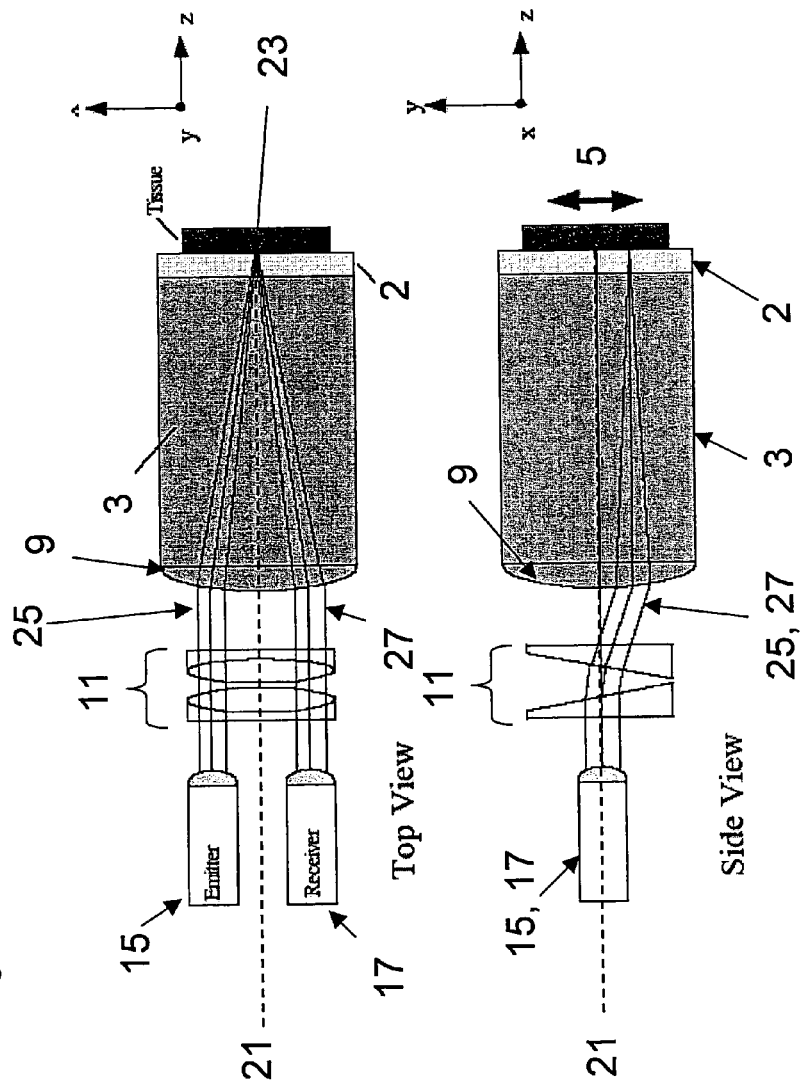
FIGS. 2a and 2b show top and side views respectively of the optical system of the probe.
Figure 2C:
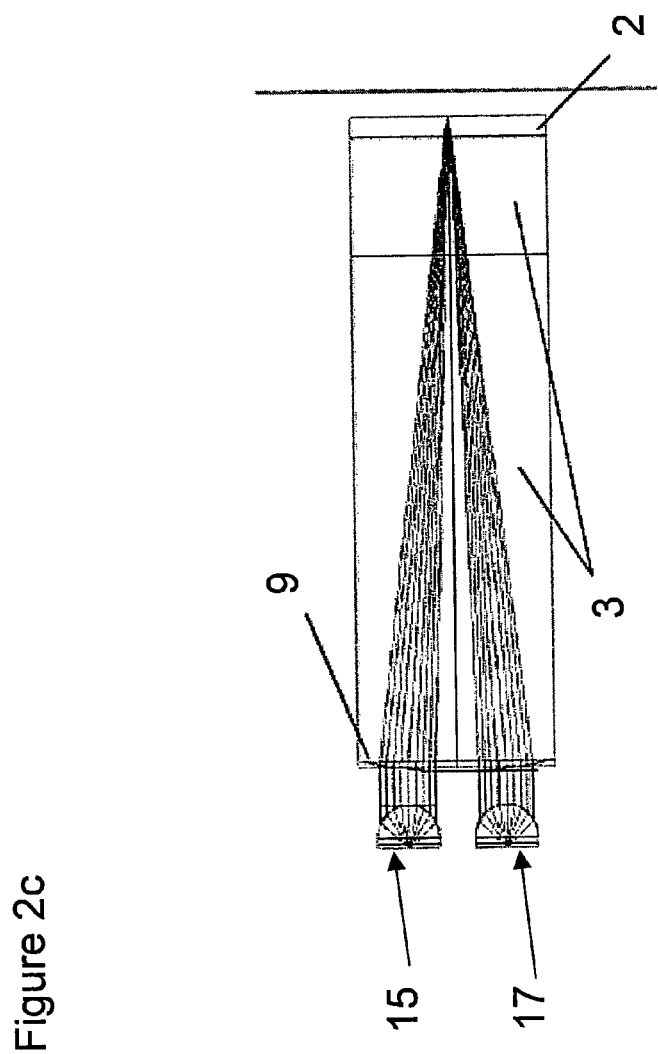
FIG. 2c shows further detail of the optical system viewed from above.

FIG. 2 shows the relative positioning of the probe's components in detail. FIG. 2a shows a top view of the probe, while FIG. 2b shows a side view. The emitter 15 and receiver 17 cartridges are positioned either side of the central axis 21 of the probe, and are equally distant from the central axis 21. The central axis 21 is coincident with the optical axis 21 of the hemispherical lens 9 and is parallel to the first probe direction 5. The separation from the optical axis 21, combined with the effect of passage through the lens, has the net effect that collimated radiation 25 emitted from the emitter 15 will be both focussed and deflected by the lens 9. The deflection will be such that the radiation emitted by the emitter 25 will be focussed at a spot 23 on the quartz window, and that radiation that undergoes a specular reflection from this spot 23 will propagate back through the dielectric member 3. The angle at which the reflected radiation 27 propagates through the dielectric member 3 will be equal and opposite to that made by the incident radiation to the optical axis of the lens 21 after the emitted radiation 25 has passed through the lens 9. Thus, when the reflected radiation 27 encounters the lens 9, the reflected radiation 27 will be collimated into a beam. The centre of the beam of radiation will be equally spaced from the optical axis 21 of the lens as the transmitted radiation 25. The receiver cartridge 17 is thus ideally located to collect the collimated, reflected radiation 27.

FIG. 2b shows a side view of the relative positioning of the THz probe's components. In the vertical direction, the emitter 15 is positioned such that the emitting aperture is centred on the optical axis 21 of the lens. Similarly, the receiving aperture of the receiver 17 is also centred on the optical axis 21.

Each Risley prism in the pair 11 comprises a wedged transmissive optic. When THz radiation passes through the first wedged optic, the radiation is deflected in a direction that is dependent on the angle that the normal to the wedged surface makes with the incident radiation. On passage through the second optic in the pair 11, the THz radiation will again be deflected by some angle. By counter-rotating the two Risley optics at equal rates, the net deflection produced by the Risley prism pair 11 can be controlled such that it acts in the vertical direction only, and varies in magnitude with the rotation of the prism pair 11.

This variable deflection will subsequently result in the focal position 23 of the THz radiation describing a line on the quartz window 2 as the deflection provided by the Risley prism pair is varied. This thus provides a linear scan of focussed THz radiation across the quartz window 2. The focussed spot size of the THz radiation is approximately 1 mm in diameter. The technique of using Risley prism pairs to provide linear scans is described in greater detail in GB2414294.

The Risley prism pair 11 also includes means to determine the time at which a rotation of the prisms 11 has been completed. The data processing system can use this timing information to determine the correct location of data within each scan.

THz radiation emitted 25 from the emitter 15 will be deflected by the Risley prism pair 11 and propagate through the lens 9 and silicon optic 3. Reflected THz radiation 27 will traverse a similar path back to the receiver 17. Since the passage of THz radiation will be fast in relation to the rate at which the Risley prism pair 11 vary the deflection of the THz beams, both the emitted 25 and reflected 27 radiation will experience essentially the same deflection, but in opposite directions. Thus, THz radiation can be scanned across the quartz window 2 and reflected back into the receiver 17. Typically, the Risley prism pair 11 are rotated at a speed of 4000 rotations per minute.

Figure 3A:
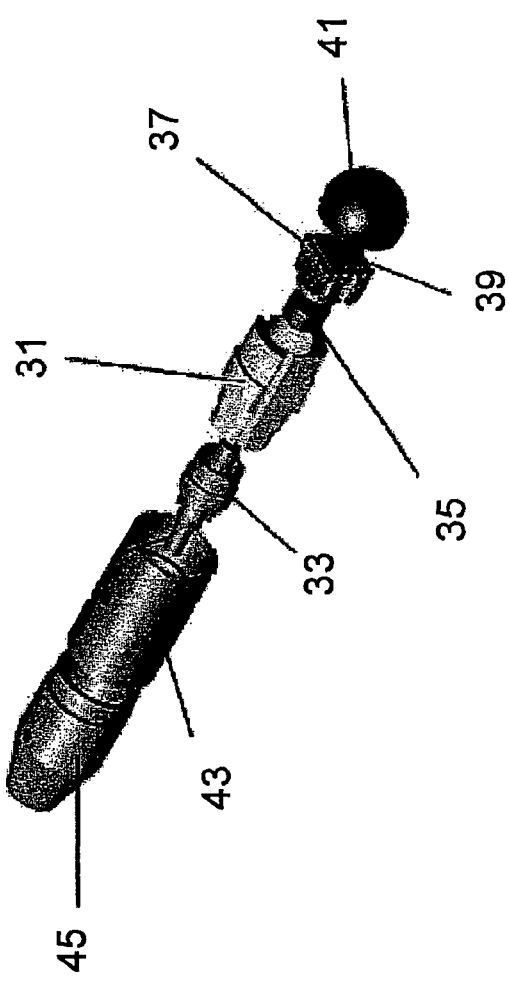
FIG. 3a shows further details of the transmitter and receiver cartridges used in the probe of the present invention.

FIG. 3a shows further detail of the emitter and receiver cartridges. Both cartridges are essentially identical in construction. The cartridge body 31 has a first end which is suitably adapted to mate with a fibre ferrule 33. The fibre ferrule 33 comprises the termination of an optical fibre (not shown) that delivers optical pump radiation to the cartridge. The cartridge body 31 contains a central aperture of diameter such that it allows the optical pump radiation to pass axially through it. Located on the opposing end of the cartridge body 31 to the fibre ferrule 33 is an aspherical lens 35. The aspherical lens 35 has its optical axis centred on the axis of the cartridge body 31. The positioning and focal length of the aspherical lens are such that optical pump light emanating from the optical fibre is first collected and then refocussed by the lens 35. The direction from the first end of the cartridge body 31 to the aspherical lens defines the forward direction of the cartridge. A GaAs antenna 39 is located at the re-imaging point of the aspherical lens. In the case of the emitter cartridge, this antenna 39 serves to emit THz radiation, while in the case of the receiver cartridge the antenna 39 detects THz radiation. The mechanisms of emission and detection of THz radiation are explained in greater detail below in relation to FIGS. 4 and 5.

The antenna 39 is mounted on a leadless chip carrier (LCC) 37, which is located between the aspheric lens 35 and the antenna 39. The LCC 37 also has an aperture such that the pump radiation is able to pass through the LCC 37 it and on to the antenna 39. The LCC 37 serves to provide means to establish electrical connection to the antenna 39 and also means to mount the antenna at the position as described above.

In the case of the emitter, a silicon lens 41 is positioned such that it collects forward generated THz radiation. The THz radiation generated by the emitter will be divergent, and the silicon lens 41 has a focal length chosen such that the lens 41 collimates the collected THz radiation.

In the case of the receiver, the lens 41 is located in the same position. As a result, collimated THz radiation that impinges on the lens 41 in the backward direction will tend to be focussed to a spot on the receiver antenna.

The ferrule 33, cartridge body, 31, aspheric lens 35, LCC 37, antenna 39 and Silicon lens 41 are all contained within a cylindrical outer casing 43. The front of the casing is formed by the silicon lens 41, while the back of the casing is formed from a tapered cylindrical member 45 that has an axial hole to allow an optical fibre (not shown) to enter the rear of the casing 45.

Figure 3B:
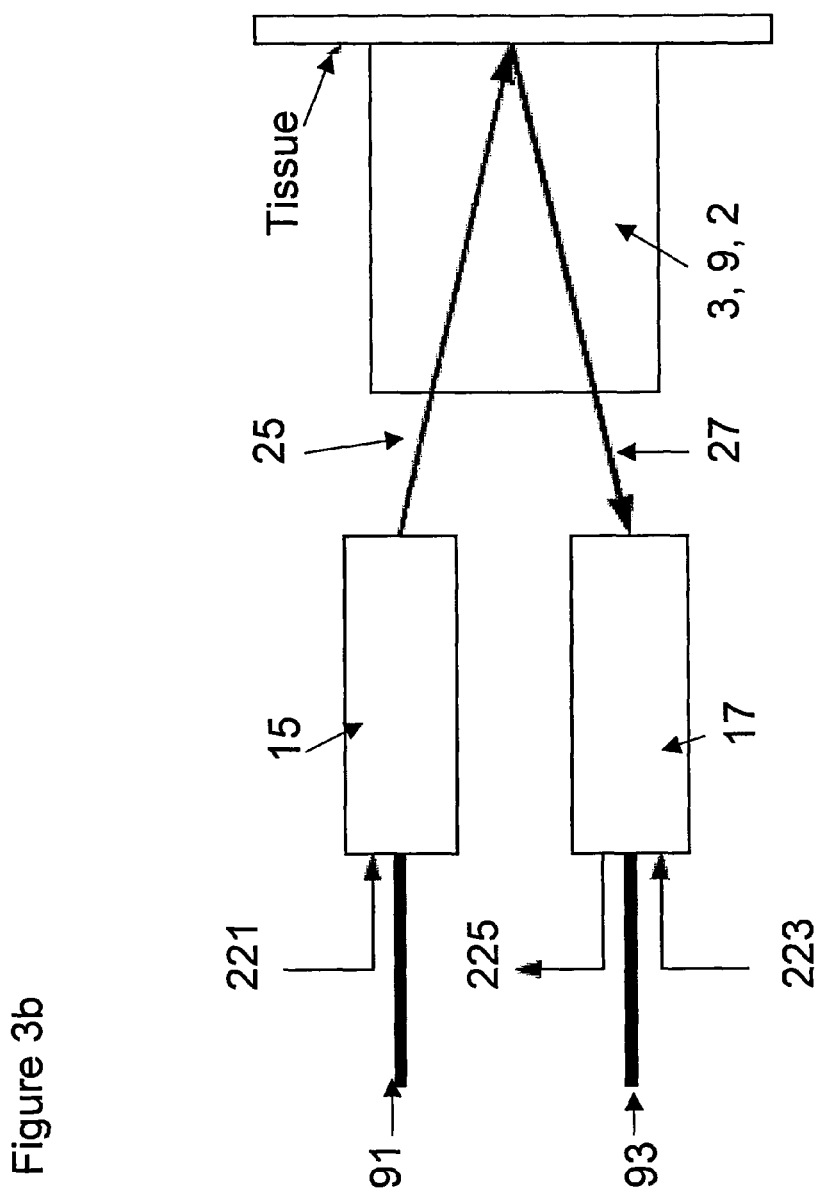
FIG. 3b shows the electrical and optical connections provided to the transmitter and receiver cartridges.

FIG. 3*b* shows the electrical and optical connections to the transmitter and receiver cartridges. Each cartridge is provided with short pulse optical radiation that is delivered via an optical fibre 91, 93. The function of the optical radiation is described in further detail below. Also supplied to the emitter 15 is a bias voltage via electrical connection 221, while the electrical signal detected by the receiver is delivered to the processing system via an electrical connection 225. The receiver cartridge 17 is further supplied with a D.C. voltage, delivered via an electrical connection 223. The electrical supply 223 provides power to drive an electrical circuit located in the receiver cartridge 17. This circuit includes a high impedance buffer amplifier to prevent excessive loading to the receiver antenna 39.

Figure 4:
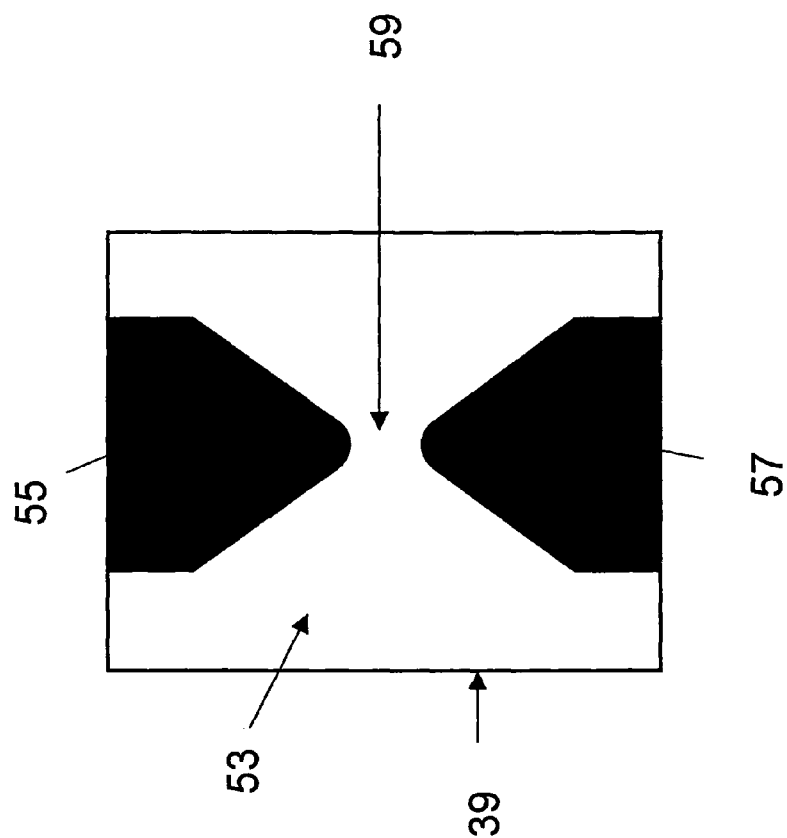
FIG. 4 shows detail of a 'Bowtie' type photoconductive antenna used in the transmitter and receiver devices.

FIG. 4 shows a schematic view of a design for the antenna 39 known as a 'Bowtie' type antenna. This antenna is described for example in GB2393037. The antenna 39 may be configured as either an emitter or a detector.

The photoconductive antenna comprises a photoconducting substrate 53. Two electrodes 55, 57 are provided on a surface of said substrate 53. The electrodes 55, 57 are generally triangular in shape and are arranged in mirrored relation with their apexes facing. The apexes being spaced apart by photoconducting gap 59. The facing apexes are blunted or rounded.

Both generation and detection of radiation, particular Terahertz radiation, can be effected using short duration optical pulses, which are inherently broadband and rely on ultra-fast lasers, a sub-picosecond optical/NIR laser pulse of appropriate wavelength is directed onto the photoconductive antenna of FIG. 4.

Upon exposure of the substrate 53 to a pulse of suitable wavelength, the conductivity of the substrate increases by a large factor, such that current flows through the material between the electrodes 55 and 57, due to the presence of the bias electric field applied between the electrodes. The photo-generated transient current radiates in a broadband with frequencies up to the Terahertz range. The current will persist for a time corresponding to the "lifetime" of the photo-created charge carriers in the material, provided that the bias field is maintained. Normally, the lifetime of the photo-generated charge carriers will be considerably longer than the duration of the incident optical pulse, will is normally of sub-picosecond duration. Thus, the generated pulse of THz radiation will have a duration that is also considerably longer than the optical pulse duration.

For detection, the photoconductive antenna 39 is operated in a similar fashion to the above. The photoconductive antenna 39 is again irradiated using either a sub-picosecond optical/NIR laser pulse of appropriate wavelength or by two CW lasers of slightly differing frequency. In addition, the radiation to be detected is directed onto the reverse side of the antenna 39. When radiation is present, current flows between the electrodes, this current can be measured in order to indicate the presence and strength of the incident radiation.

The choice of photoconductive material for such emitters and detectors generally depends upon the laser excitation source. Gallium Arsenide (GaAs) is particularly useful, as its band-gap matches well to Ti:Sapphire laser wavelengths and also to laser diode wavelengths. Ti:Sapphire lasers are commonly used in both pulsed and CW systems and laser diodes are commonly used in CW systems. Therefore the photoconductive material is chosen so that the material has a band-gap that is suitable for the wavelength of the laser.

Figure 5:
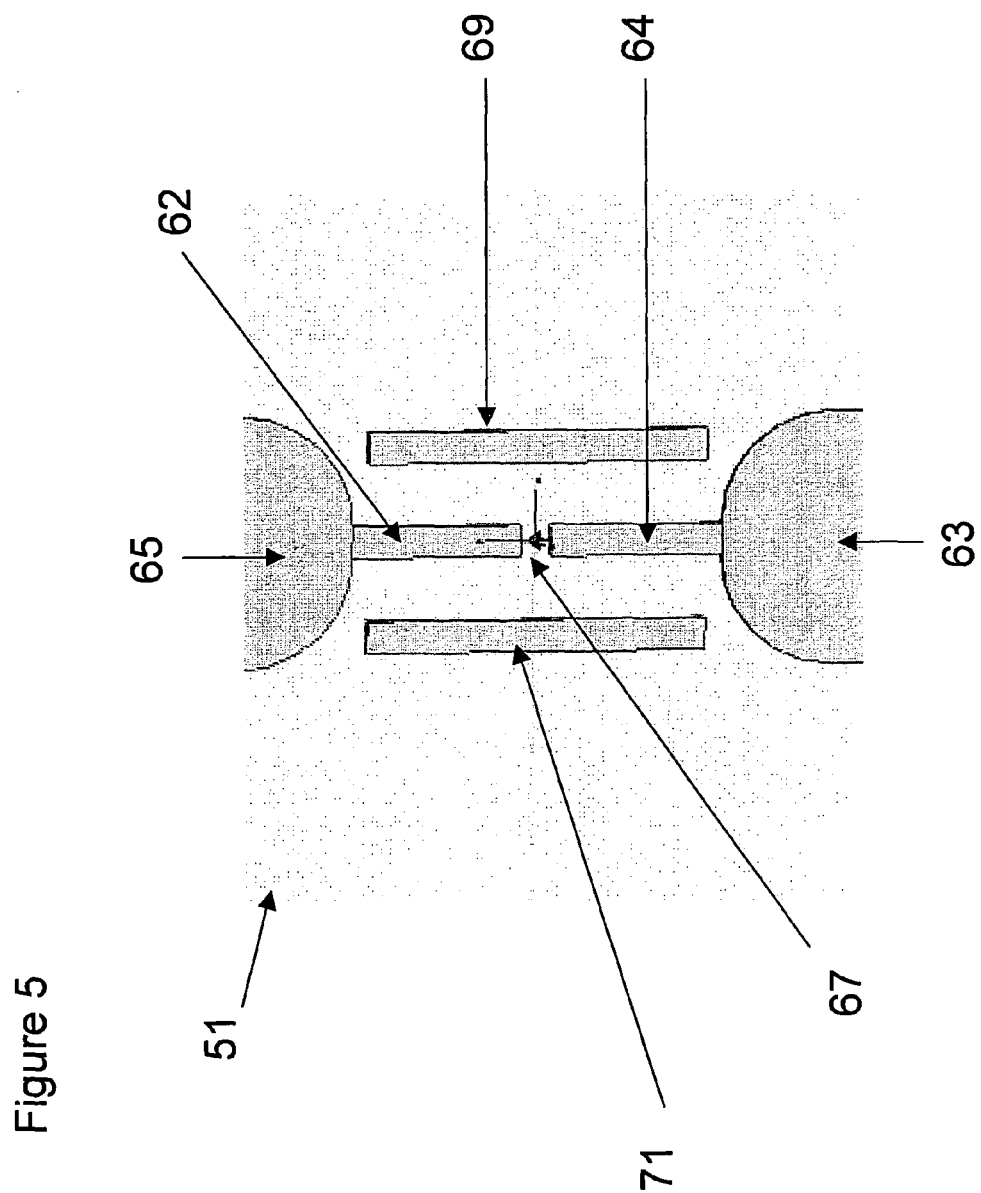
FIG. 5 shows details of alternative, resonant, photoconductive antenna for use as the transmitter and/or receiver devices.

FIG. 5 shows a schematic view of an alternative, improved, antenna 39 design, called a resonant antenna. The antenna chip 61 is also made from a photoconductive material, such as, GaAs and consists of a planar sheet of material. The rear surface of the sheet is illuminated by optical pump light as described above for FIG. 3. In the case of the emitter antenna THz radiation is emitted from the front face of the antenna chip 61, while in the case of the receiver, THz radiation is incident on the front face for subsequent detection.

The antenna is defined by gold metalisation on either the front or rear surface, typically the metalisation will be of thickness 300 nm. Two collinear rectangular strips of metalisation 62, 64 each 1 µm wide and 5.5 µm long with a gap 67 between them of 1 µm form the two poles of the antenna. The gap 67 between the poles of the antenna defines the active region of the antenna, and this is the point where the incident pump radiation is predominantly incident. At the outer end of each antenna pole 62 64, further regions of metalisation 63, 65 firm contact pads for the antenna poles 62, 64. These contact pads 63, 65 are rectangular strips 8 µm wide, each having one arcuate end of radius 7 µm. The contact pads 63, 65 are positioned such that they each form contact with the outer end of one of the antenna poles 62, 64 via their arcuate ends. The contact pads 63, 65 are aligned such that their long sides are parallel to the antenna poles 62, 64. The design of the antenna poles 62, 64 and contact pads is such that a low-impedance coupling is achieved between the antenna poles and their respective contact pads.

To provide the resonant enhancement to the antenna, two further strips of metalisation 69, 71 are positioned one either side of the antenna poles 62, 64. The resonant enhancement strips 69, 71 are rectangular strips 1 µm wide and 11 µm long. The resonant enhancement strips have their long side orientated parallel to the antenna poles 62, 64, and are separated from the poles by a distance of 2 µm, with one strip positioned either side of the antenna poles 62, 64. Each resonant enhancement strip 69, 71 is positioned such that the normal to the centre of its long side passes through the centre of the gap 67 between the antenna poles 62, 64.

The process of emission or detection of THz radiation is essentially identical to that described above in relation to the Bowtie type antennas. However in the case of the resonant antenna design, the length of the resonant enhancement strips is chosen such that they have a natural frequency at a frequency of interest, in the example given above this is 2 THz. The natural frequency provides a resonant enhancement at 2 THz.

Figure 6A:
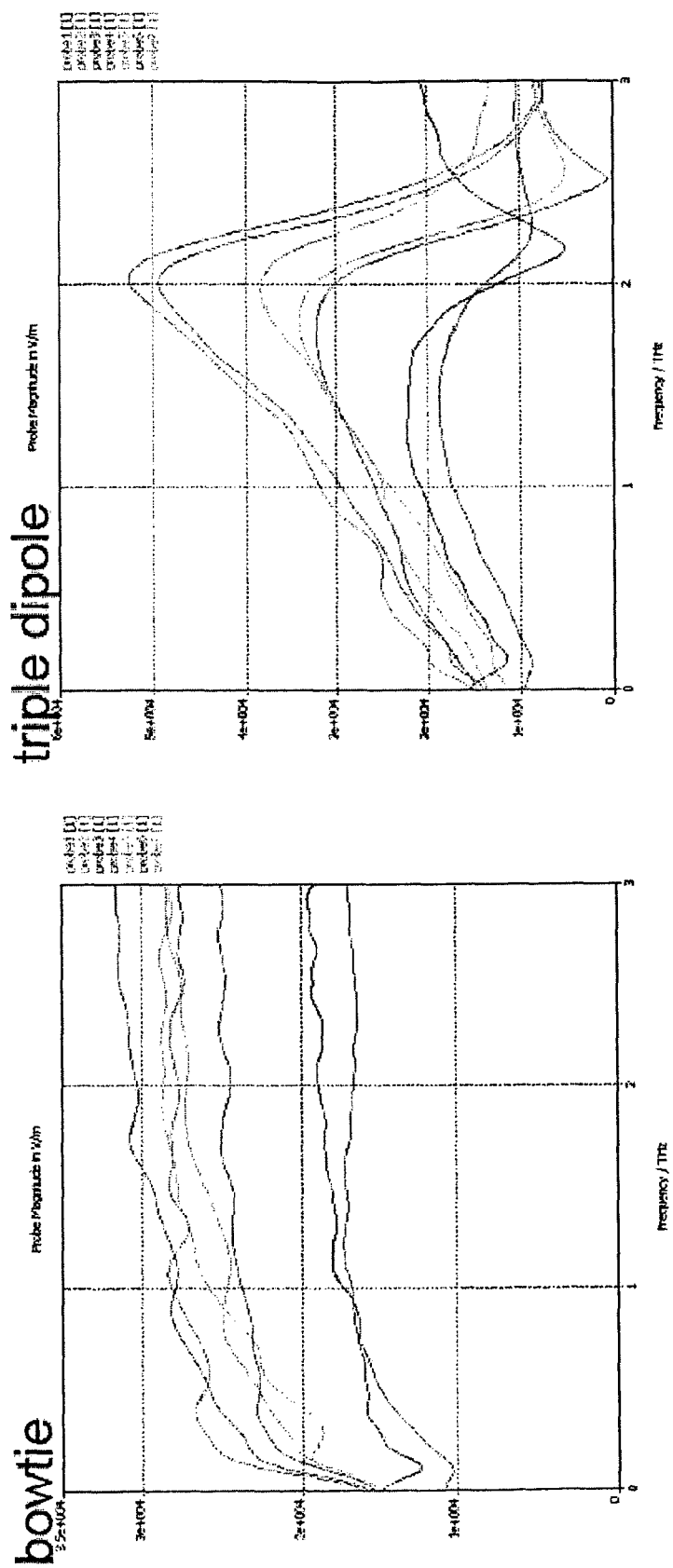
FIGS. 6a to 6h show comparisons between the performances of the two different antenna types.
Figure 6B:
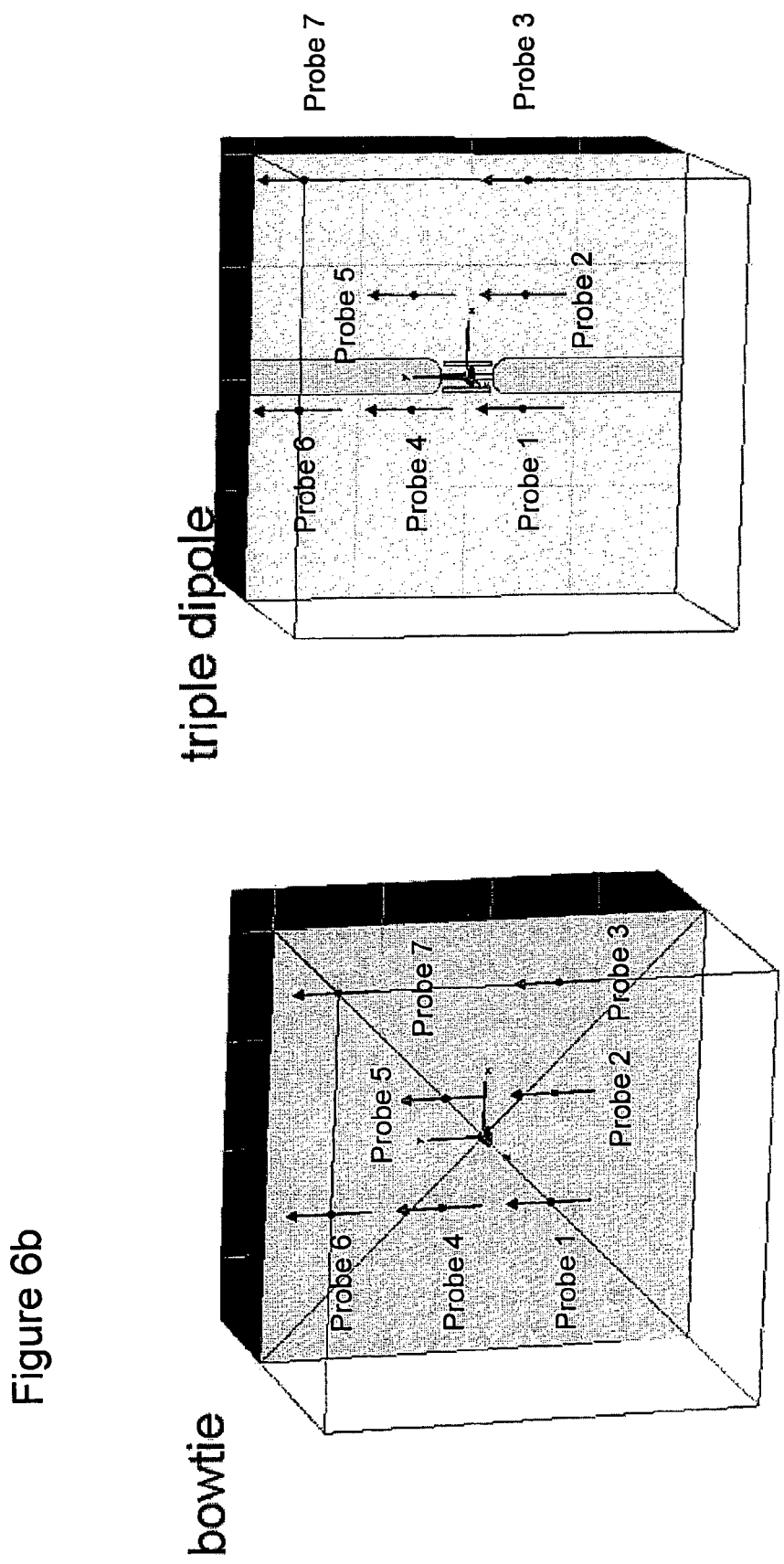

FIGS. 6a to 6h show various comparisons between the performance of the standard 'Bowtie' antenna and the resonant antenna. In FIG. 6a the magnitude of the electric field induced in the two different antenna types at various locations is compared. The probe locations as given in FIG. 6a are illustrated in FIG. 6b.

FIG. 6a shows that the resonant antenna of FIG. 5 has a clear resonant enhancement that peaks at the design frequency of 2 THz.

Figure 6C:
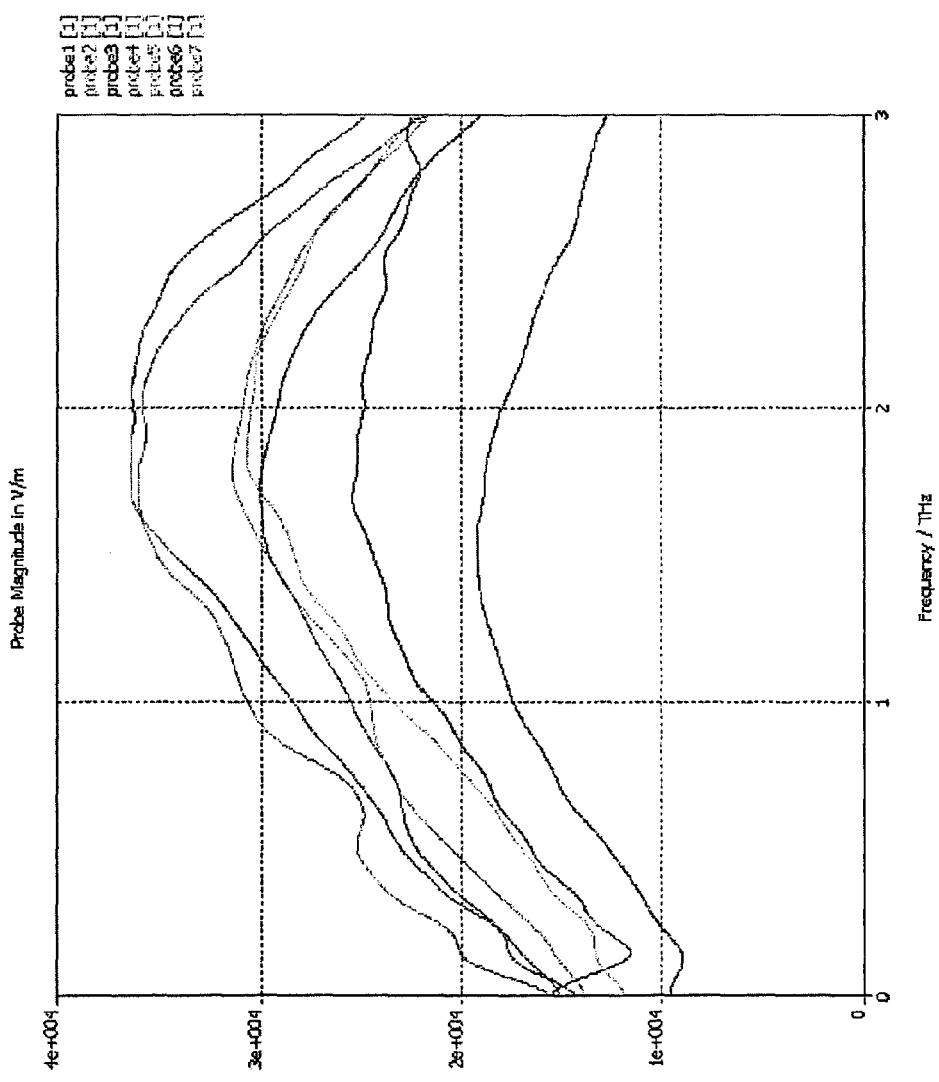

FIG. 6c shows the results obtained from the antenna of FIG. 5 that lacks the resonant enhancement dipoles 69, 71. The peak response obtained from such an antenna is lower than that obtained from the resonantly enhanced antenna of FIG. 5.

Figure 6D:
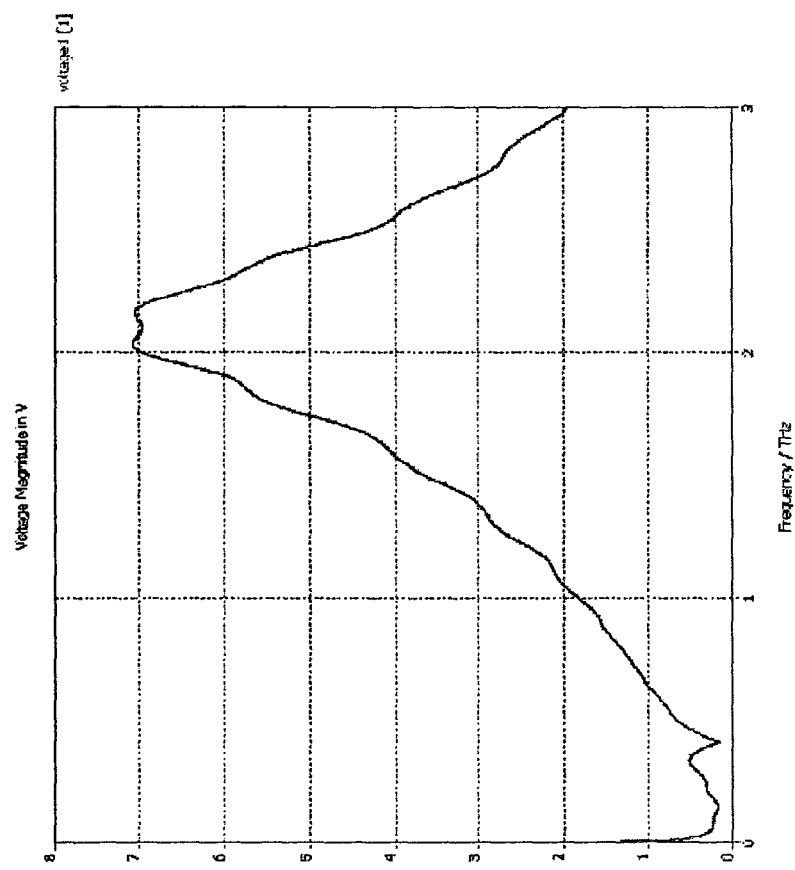

FIG. 6d shows the measured Q-factor of the antenna described above for FIG. 6c. The Q-factor is a measure of the resonant enhancement provided by the antenna design.

Figure 6E:
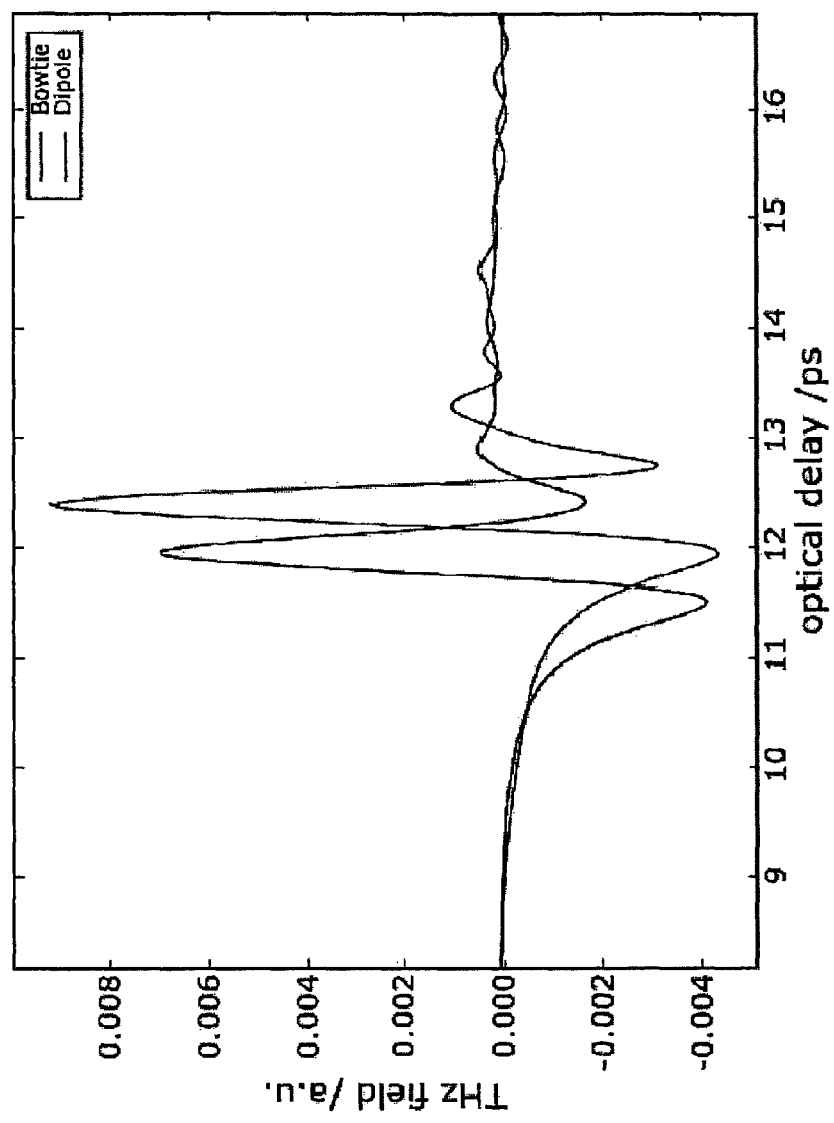

FIG. 6e shows a comparison of the two antenna designs when used as emitters of THz radiation. The resonant type antenna, labelled in the figure as 'dipole' generates a larger electrical field in the THz regime than the standard or 'bowtie' type antenna.

Figure 6F:
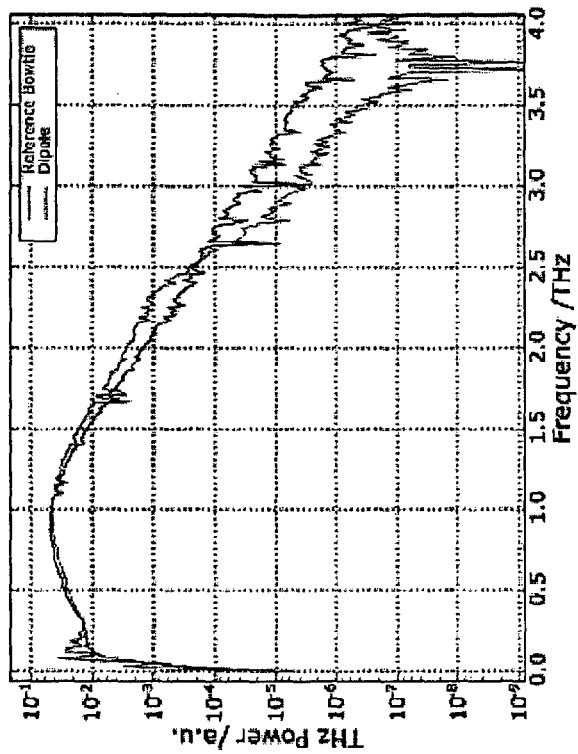
Figure 6F:
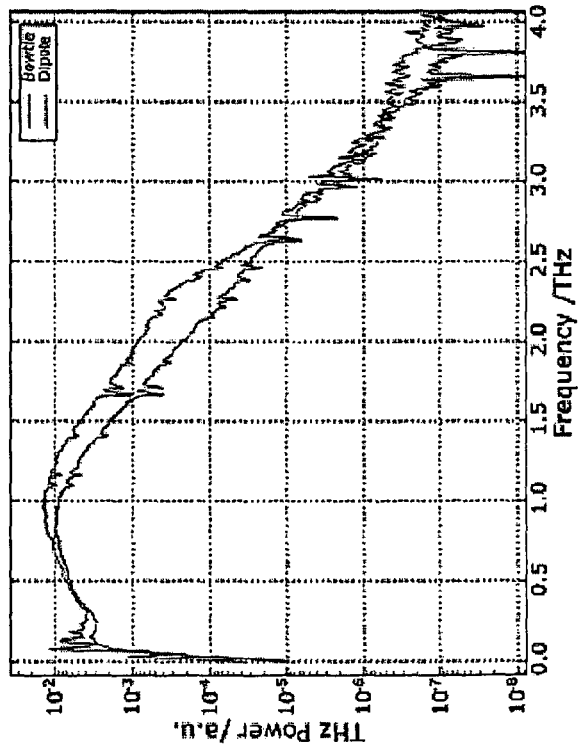

FIG. 6f shows a comparison of the two antenna designs in terms of their spectral performance when acting as emitters of THz radiation. The figure shows that the resonant type antenna generates higher electrical fields at all frequencies up to 2.5 THz.

Figure 6G:
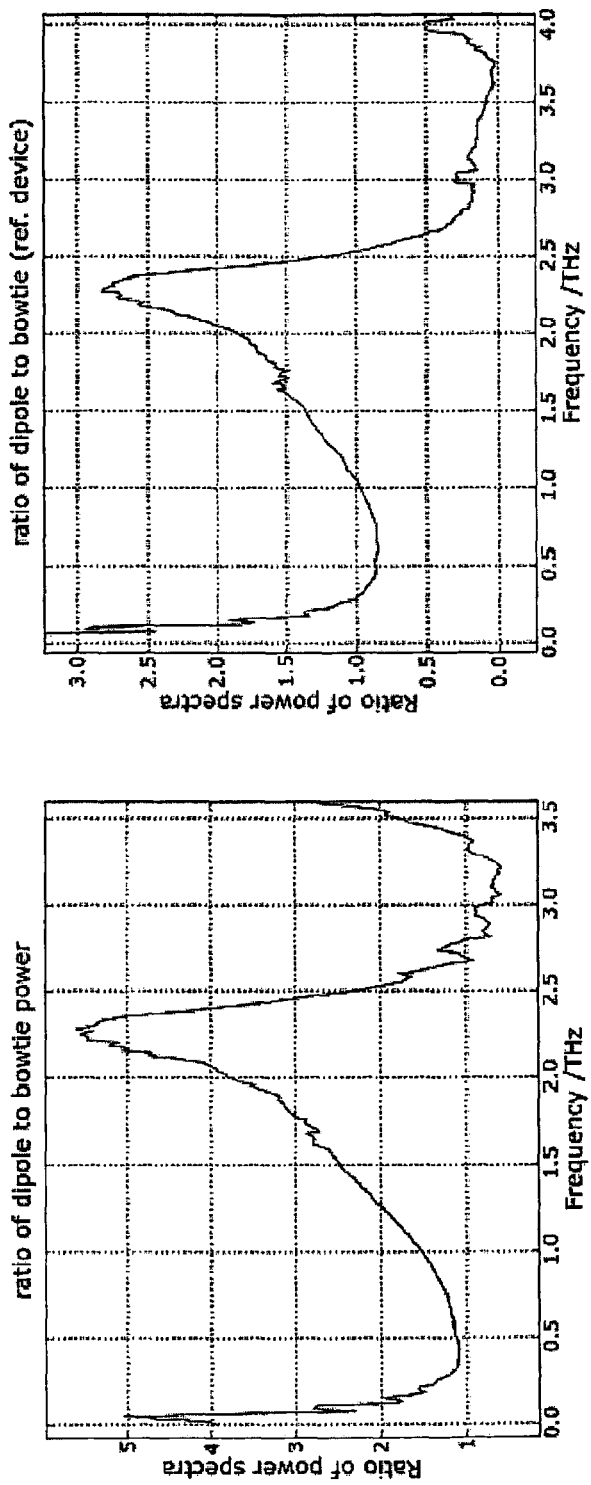

FIG. 6g shows an alternative presentation of the data shown in FIG. 6f, wherein the ratio of the electrical fields produced by the two antenna types is shown.

Figure 6H:

FIG. 6h shows a comparison of the near infrared excitation of the two antenna types when pumped with short-pulsed optical radiation.

Figure 7:
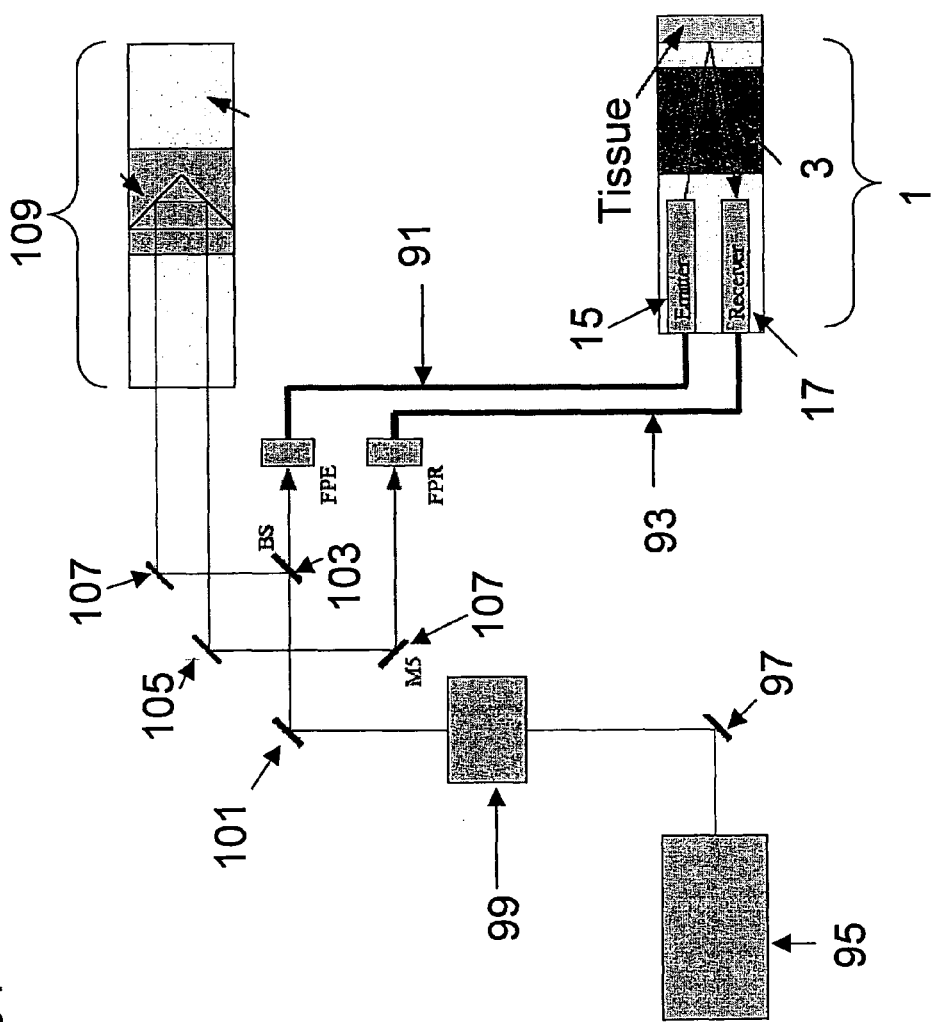
FIG. 7 shows a block diagram of the control system for a probe in accordance with the present invention.

FIG. 7 shows a schematic view of the optical system used to drive a THz system, including the probe 1. The probe 1 has fibre optic connections 91, 93 that deliver optical radiation to the emitter 15 and receiver 17 respectively. The optical radiation is provided by a laser 95, and takes the form of broadband ultrashort pulses with a wavelength that is centred in the near Infrared. Typically, pulses of duration 100 fs are used. The optical pulses from the laser 95 are directed by a mirror 97 into a dispersion compensation system 99. The dispersion compensation system 99 pre-compensates for the dispersion that will later occur as the optical pulses propagate through the optical fibres 91, 93. Unless compensation is applied, the dispersion that occurs on propagation through the fibres 91, 93 will tend to cause the optical pulse duration to lengthen. Such a lengthening of the pulse duration would have detrimental consequences for the production of THz radiation.

After exiting the compensator 99, the optical radiation is incident on another mirror 101, which directs the radiation onto an optical beam splitter 103. The beam splitter 103 divides the incident radiation into two portions. One portion is immediately launched into the optical fibre 91 connected to the emitter 15. The remaining radiation is incident on another mirror 107, which then directs the radiation into a variable delay line 109.

The delay line 109 shown in FIG. 7 comprises a prism retroreflector on a translation stage, however alternative delay lines may be used, and such an alternative delay line is described in greater detail below. The beam splitter 103 may either divide the incident radiation by polarisation or by amplitude.

On exiting the delay line 109, the radiation is incident on two further mirrors, 105, 107 which serve to direct the radiation so that it is launched into the optical fibre 93 connected to the receiver 17. By splitting the radiation from the laser in this way, a variable optical path length difference can be established between the radiation arriving at the emitter 15 and receiver 17.

Figure 8:
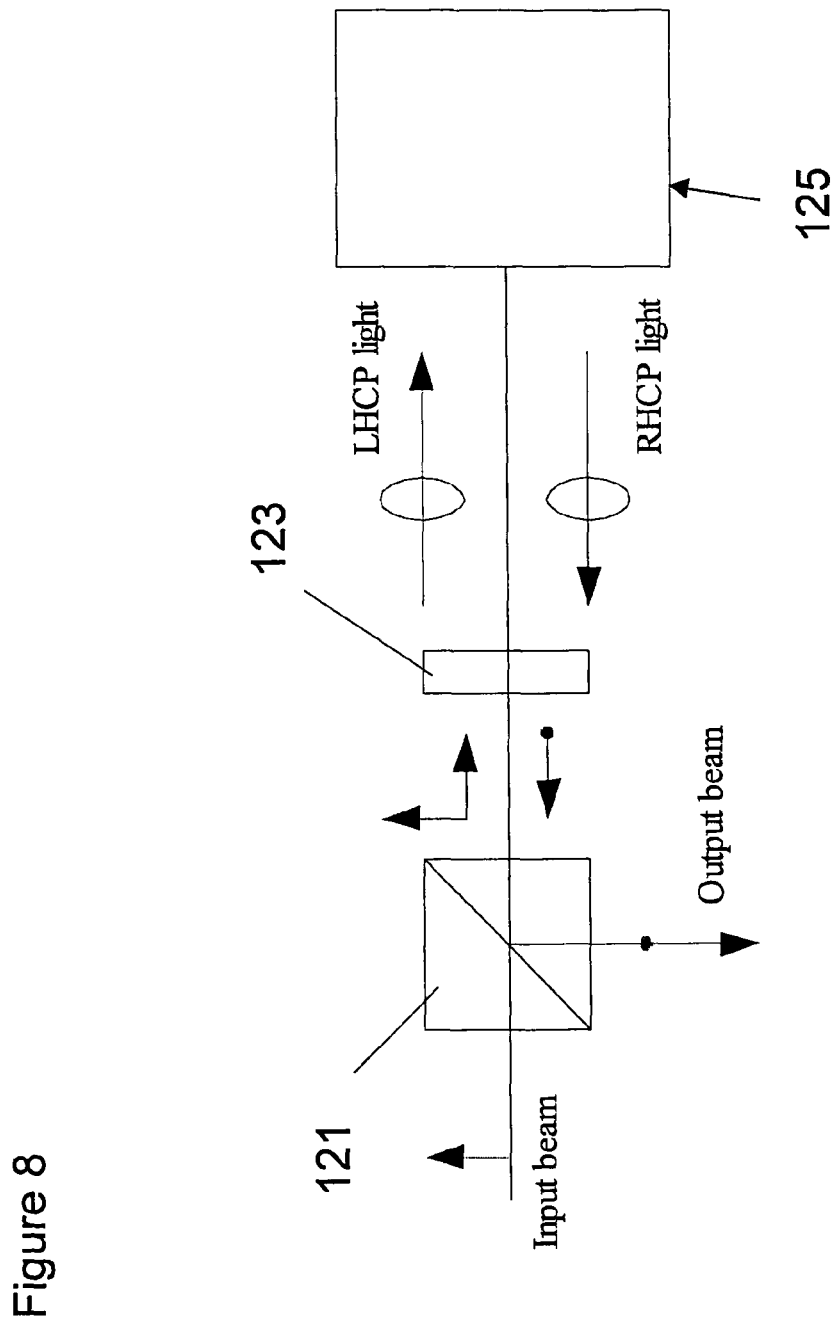
FIG. 8 shows detail of the variable optical delay line used in the system.
Figure 9:
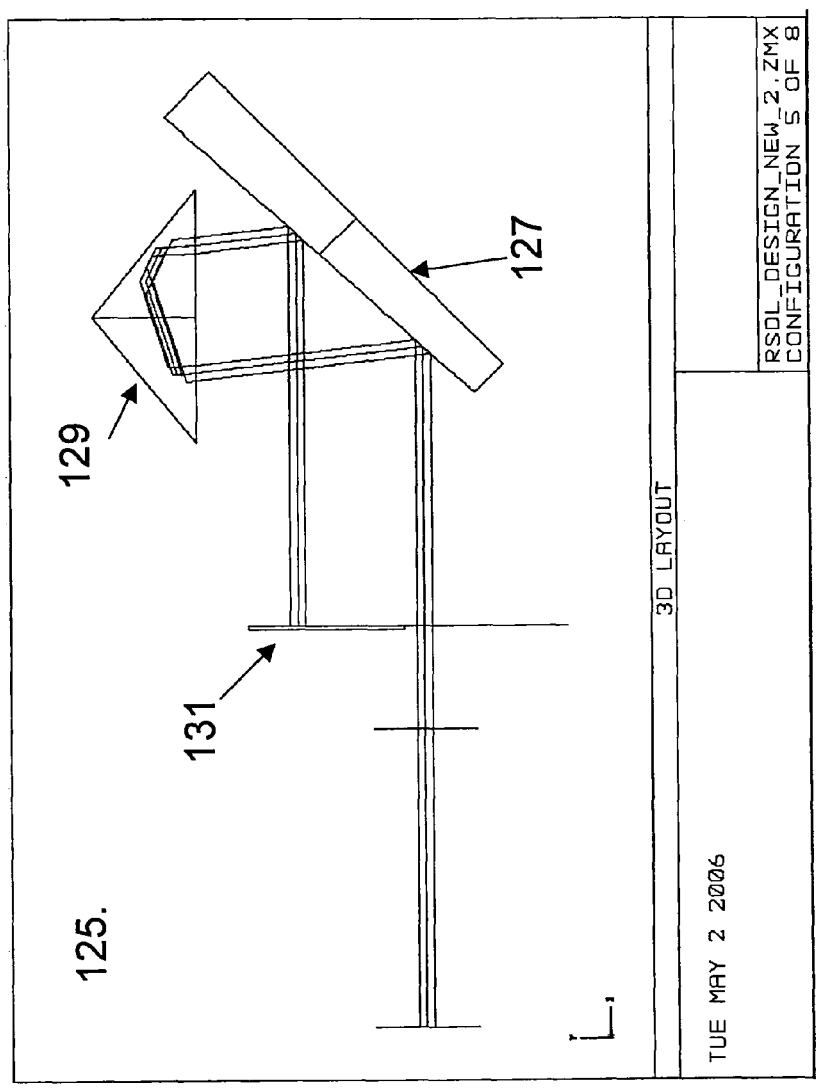
FIG. 9 shows further detail of the variable optical delay line.

An example of a suitable variable delay line 109 is shown in detail in FIGS. 8 and 9. In FIG. 8, the light entering the delay line 109, is first incident on a polarising beam splitter 121. Conveniently, the incident light will be linearly polarised in a direction such that the polarising beam splitter 121 allows passage of the radiation. On transmission, the light is then incident on a quarter wave plate 123. The quarter wave plate 123 is oriented such that it converts the incident, linearly polarised, light into circularly polarised light. Subsequently, the circularly polarised light enters the rapid scan delay line (RSDL) 125. This device is described in greater detail below however, the structure of the RSDL 125 is such that light is retro reflected from it with a variable delay and with a circular polarisation state that is of the opposite handedness to the incident light. Thus, if left circularly polarised light is incident on the RSDL 125, the returning light is right circularly polarised. The retro-reflected light is then incident for a second time on the quarter wave plate 123. Due to the change of polarisation state between the incident and retro-reflected light, the retro-reflected light is converted to linearly polarised light that is orthogonally polarised to the incident light. Thus, when the retro-reflected light is again incident on the polarising beam splitter 121, the beam splitter acts to deflect the retro-reflected light. The retro-reflected light can thus be separated from the incident light.

FIG. 9 shows detail of the RSDL 125. The RSDL 125 contains a wedged mirror 127 that is formed on a substrate that has a small angle between its front and back surfaces, and is reflective on its front surface. The wedged mirror 127 is placed in the path of the incoming light such that the back surface makes an angle of approximately 45° with the incident light. Light reflected from the mirror's front surface is thus deflected by an angle of approximately 90°, with a small variance from this being caused by the wedge angle of the mirror 127. A corner-cube retro reflector 129 collects the reflected light. Due to the nature of retro reflection from corner-cube devices, light is retro reflected anti-parallel to the incoming light and displaced by an amount that is dependent on the position on the corner-cube retro reflector 129 at which the light was incident. Thus, the retro reflected light will be directed back onto the mirror 127, incident at the same angle at which it was reflected but in a different location on the mirror's surface. The mirror 127 will again reflect the light, this time such that it will be anti-parallel to the light as it entered the RSDL 125. A plane mirror 131 is positioned in the path of this light, such that the light is incident at normal incidence to the mirror's surface. The light is thus retro reflected again by this mirror 131, and so retraces it's path through the RSDL.

The wedged mirror 127 is configured to rotate about an axis that is central to the mirror 127 and normal to the back surface of the mirror 127. Due to the wedged nature of the mirror 127, the optical path length of the above described path will vary on rotation of the mirror 127. Thus, by rotating the mirror a variable optical delay can be generated.

Figure 10:
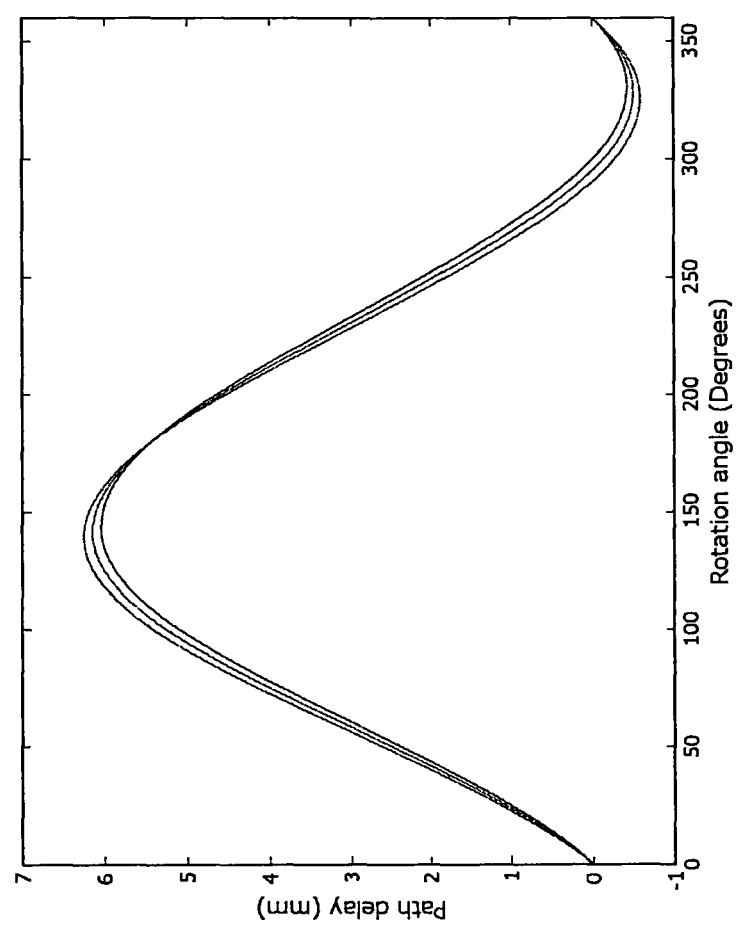
FIG. 10 shows the optical delay achieved during a scan of the delay line.

FIG. 10 shows the variable optical path delay generated when rotating a mirror with a wedge angle of 3.25° used in the above described RSDL through a full turn. As can be seen from the figure, the variation is sinusoidal in nature.

Figure 11:
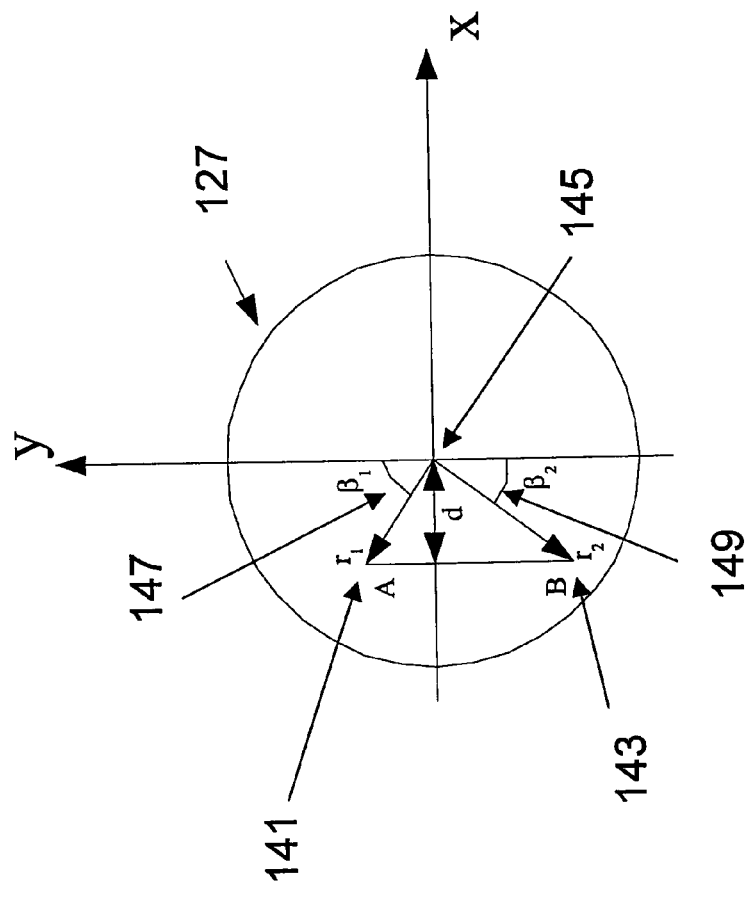
FIG. 11 shows the relative positions on the wedged mirror of the optical delay line at which the optical beam is incident.

FIG. 11 shows a diagram of the points on the wedged mirror 127 from which the incoming and returning light are reflected. Point A 141 is taken to be the point at which the incoming light is incident, while point B 143 is the point at which the returning light is incident. Taken with the axis of rotation 145, these points describe a triangular shape on the surface of the wedged mirror 127. The amplitude of the path delay will depend on the distance of each of these points from the axis of rotation 145. The amplitude of the path delay will also depend on the angles 147, 149 defined by the directions from the axis of rotation 145 to the points of reflection 141, 143. These angles being measured in relation to the horizontal and vertical directions. In particular, the two angles 147, 149 must both be greater than zero to ensure that the delay achieved is non-zero.

At each reflection of an electromagnetic wave from a material with a higher refractive index than the material in which the wave is propagating, a phase change of $\pi$ radians is introduced into the reflected radiation. The introduction of a phase change of $\pi$ radians to circularly polarised light results in the handedness of the polarisation being changed. Thus, if the incident light was right-circularly polarised, then the reflected light will be left-circularly polarised and vice versa.

In the above described RSDL, light making a round trip path through the device experiences an odd number of these reflections, seven in total. Therefore, light that has made a round trip through the RSDL will emerge with the opposite handedness of the input light. As described above in relation to FIG. 8, this allows separation of the input and emergent light.

As the wedged mirror 127 rotates, the reflective surface presents a variable angle to the incoming/returning light. As a result, the polarisation state of the light is changed on reflection. The polarisation state changes from circularly polarised to elliptically polarised. Additionally, the corner cube reflector 129 will tend to exhibit similar effects on the polarisation state of the incident light. As a result of this, the returning light will not be circularly polarised, and the polarisation state of the returning light will vary over the rotation of the wedged mirror.

In an attempt to overcome the above polarisation effects, the system was mathematically modelled. The effects of the wedged mirror 127 and polarisation sensitivity were modelled separately to simplify the process.

Firstly, it was assumed that the wedged mirror 127 had a wedge angle of 0°. The system was then modelled using Jones matrices and, using this notation, the effect of an optical element on the polarization state of a beam can be written as:

$$\begin{bmatrix} E_{xout} \\ E_{yout} \end{bmatrix} = \begin{bmatrix} m_{11} & m_{12} \\ m_{21} & m_{22} \end{bmatrix} \begin{bmatrix} E_{xin} \\ E_{yin} \end{bmatrix} = M \begin{bmatrix} E_{xin} \\ E_{yin} \end{bmatrix} \quad (1)$$

where the components of matrix M depend on the exact nature of that element. For the optical system of FIG. 8

$$\begin{bmatrix} E_{xout} \\ E_{yout} \end{bmatrix} = M_r M_{RSDL} M_f \begin{bmatrix} E_{xin} \\ E_{yin} \end{bmatrix} \quad (2)$$

where
$M_r$ represents the reverse path through the wave plate.
$M_{RSDL}$ represents the effect of passing through the RSDL.
$M_f$ represents the forward path through the wave plate.

The input light can be represented as:

$$\begin{bmatrix} E_{xin} \\ E_{yin} \end{bmatrix} = \begin{bmatrix} 1 \\ 0 \end{bmatrix},$$

Since it is desired that the output light will be circularly polarised in the opposite handedness to the input light, the desired output light can be represented as:

$$\begin{bmatrix} E_{xout} \\ E_{yout} \end{bmatrix} = \begin{bmatrix} 0 \\ 1 \end{bmatrix} \quad (3)$$

$M_{RSDL}$ may then be calculated by launching two known orthogonal polarization states (RHCP and LHCP) into the system, and using suitable optical modelling software, such as Zemax, to calculate the corresponding output polarization states.

Once $M_{RSDL}$ is known, $M_r$ and $M_f$ may then be optimized by tuning the orientation and phase delay through the wave plate, until the overall system satisfies the two conditions given in (3). This can be achieved for example using program written in Python, together with a Zemax macro.

A solution to the above does exist for the system as described in which the wedged mirror 127, corner cube retro reflector 129 and retro reflecting mirror 131 are all assumed to be coated with silver.

For the system as described above, it was found that a wave plate with a phase delay of 76.95°, with its optical axis orientated at 302.2° would result in pure circularly polarised light being output from the system if circularly polarised light of the opposite handedness were input.

Thus, preferably the quarter wave plate 123 of FIG. 8 will either be replaced by a custom wave plate with the above parameters, or it may be replaced by a combination of a half wave plate and a quarter wave plate suitably oriented to achieve the same effect.

Figure 12:
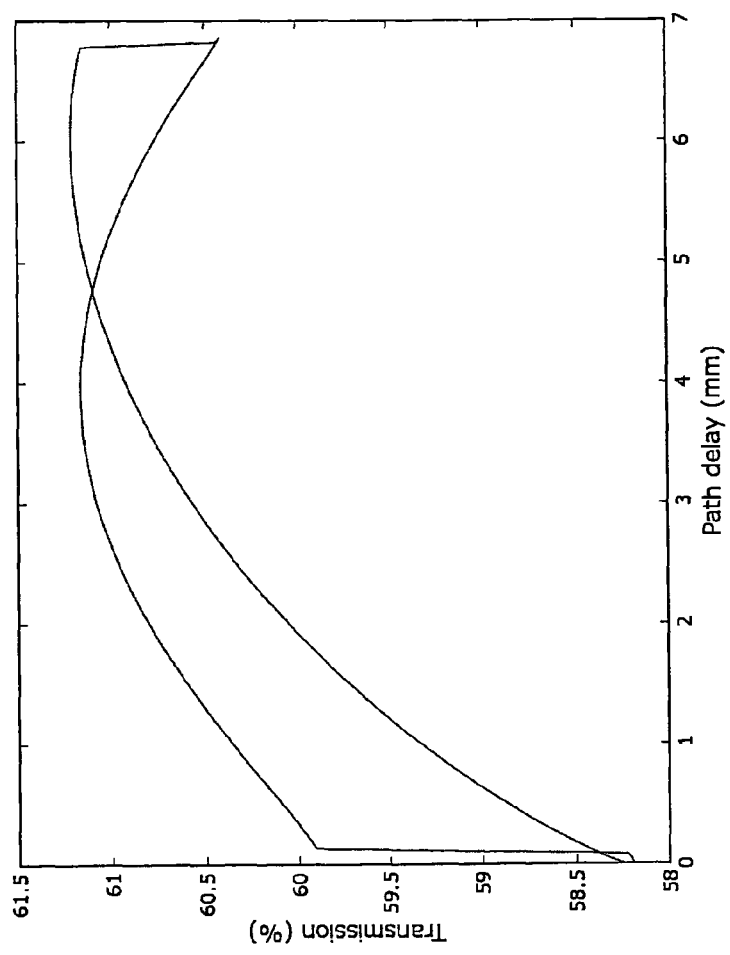
FIG. 12 shows the theoretical variation in transmission of the delay line across a scan.

The effect of the wedge angle of 3.25° in the wedged mirror 127 can be seen in FIG. 12. The effect is a variable transmission of the optical system of FIG. 8 as the wedged mirror 127 of FIG. 9 is rotated. In FIG. 12 this is plotted as transmission versus path delay, which is a function of the angle of rotation of the wedged disc 127 as shown in FIG. 10.

For the optical system as described above, there is a variation of approximately 5% in the transmission across a scan. In addition there is a discontinuity in the transmission at the extremes of the scan. Preferably, these extreme positions of the scan will be avoided when the system is in use.

Figure 13:
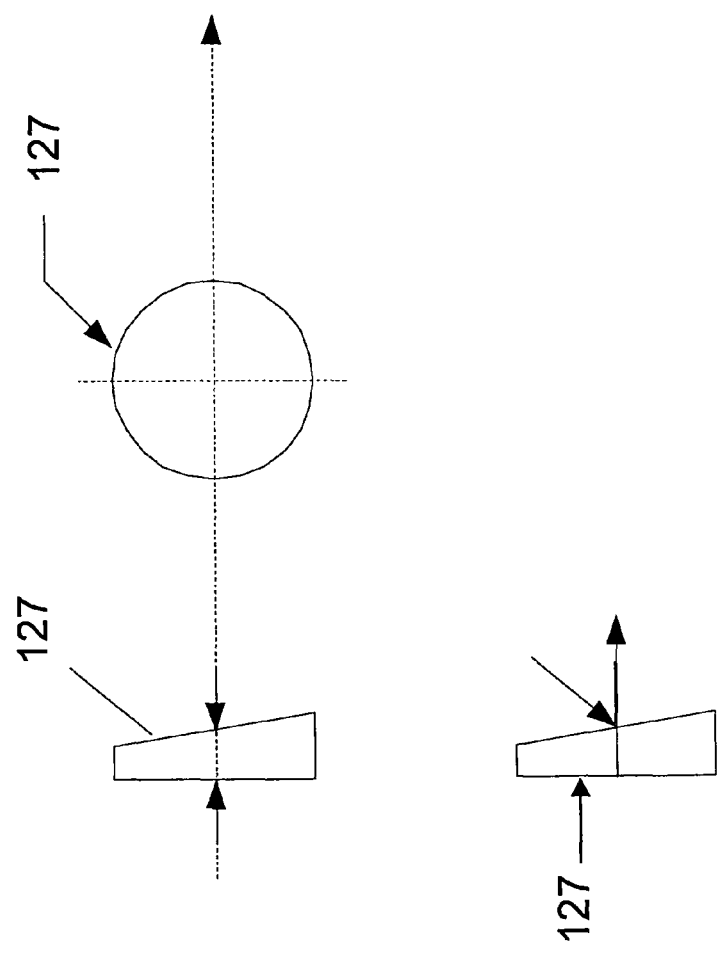
FIG. 13 shows further detail of the wedged mirror used in the optical delay line.
Figure 14:
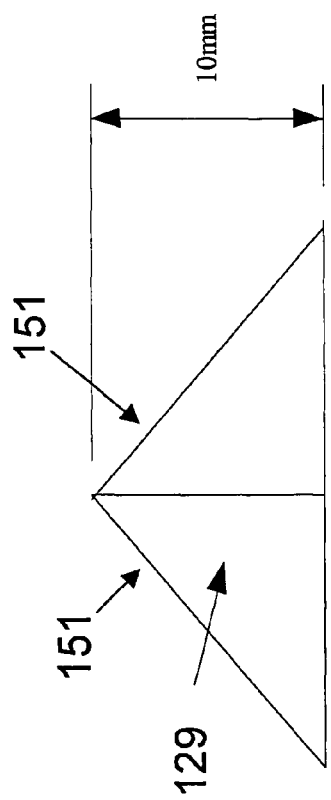
FIG. 14 shows detail of the corner cube reflector used in the optical delay line.

FIGS. 13 and 14 show further detail of the wedged mirror 127 and corner cube reflector 129 respectively.

Suitable tolerances for the wedged mirror 127 are as follows:

1) Center thickness (CT)=5 mm±0.1 mm.
2) Wedge angle=3.25+0/−0.1°.
3) Diameter=40+0.0/−0.25 mm.
4) Reflective coating=Protected silver or dielectric high reflector designed for 45° incidence. Ideally, with no relative phase delay between perpendicular and parallel field components of the incident beam to ensure that the polarisation state remains unchanged.

The RSDL 109 is designed to operate at rates of around 1 kHz. At such a scan rate, the above described wedged mirror 127 would be rotating at approximately 500 Hz, since two scans will be produced for each rotation of the wedged mirror

127. The edge velocity of the wedged mirror in this situation would be approximately 62.8 ms$^{-1}$, which is well below the speed of sound in air at sea level of approximately 340 ms$^{-1}$. Thus, there would be no sonic shockwave produced when operating at the above scan rate.

Suitable specifications for the corner cube retro reflector 129 are as follows:

1) Distance from the apex to the base of 10 mm. Tolerance on this parameter is +/−0.1 mm. All other surfaces defined with respect to this dimension.
2) Operating wavelength of 800 nm.
3) Material—BK7 or equivalent glass.
4) 2 arc second beam parallelism of reflected beam with respect to incident beam.
5) Silver coated reflecting surfaces.
6) Input face (base of corner cube) not anti-reflection coated.
7) Surface flatness λ/10 at 800 nm.
8) Chipping at base corners not critical. Important to avoid chipping at apex.
9) Chamfer to be 0.1 mm across the chamfered faces.

One of the problems with using a corner cube retro reflector 129 in the above described system is the effect of the beam passing over a facet boundary on the corner cube retro reflector 129.

A chamfer 151 will occur at all machined edges of the corner cube retro reflector 129 as indicated in FIG. 14.

Assuming a chamfer of 0.1 mm across the machined edge of the corner cube retro reflector 129, and further assuming that the optical beam used in the RSDL 109 has a wavelength of 800 nm and a Gaussian beam radius of 0.5 mm, the maximum drop in retro reflected power will be 15% as the beam crosses the boundary. This assumes that the light reflected from the bevel is lost in the system.

Figure 15:
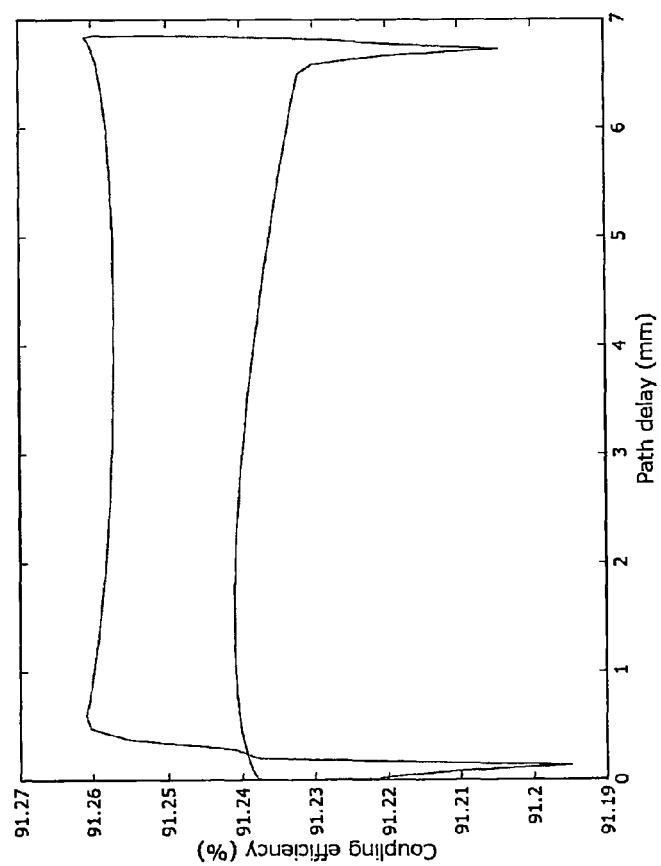
FIG. 15 shows the theoretical variation in coupling efficiency of light from the optical delay line into an optical fibre.

To determine the location where these transitions occur, a Zemax macro was written that calculated the coupled power into single mode fibre 91 from the RSDL 109 as the wedged disc 127 was rotated through one full revolution. The effect is shown in FIG. 15.

No polarization effects were included in this calculation. The transitions are noted to be at the extremes of the scan thus, with careful design of the RSDL 109, a usable scan rage of 6 mm can be achieved, albeit with a reduced effective duty cycle.

FIGS. 16 to 19 show further details of the RSDL 109.

As the wedged mirror 127 rotates, the distance between the reflective surface of the mirror 127 and the corner cube retro reflector 129 will vary due to the wedge.

Figure 16:
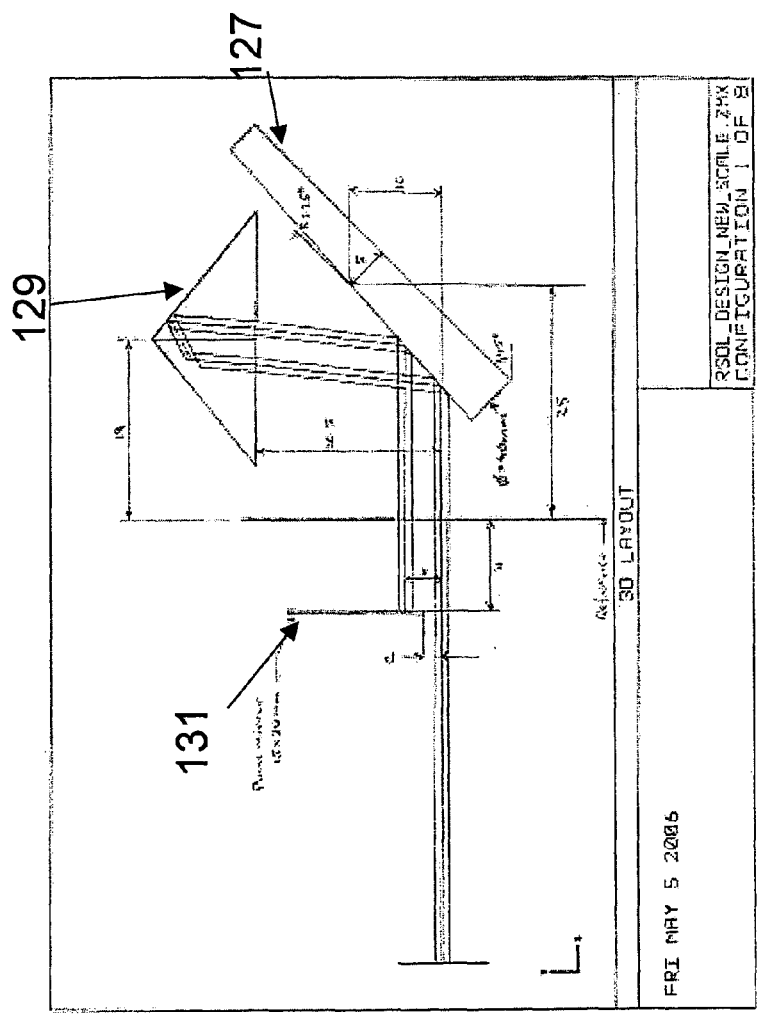
FIGS. 16 to 19 show further details of the optical delay line.

FIG. 16 shows a side view of the RSDL 109 with the wedged mirror 127 in the rotational position where the gap between the wedged mirror 127 and the corner cube retro reflector 129 is at its maximum.

Figure 17:
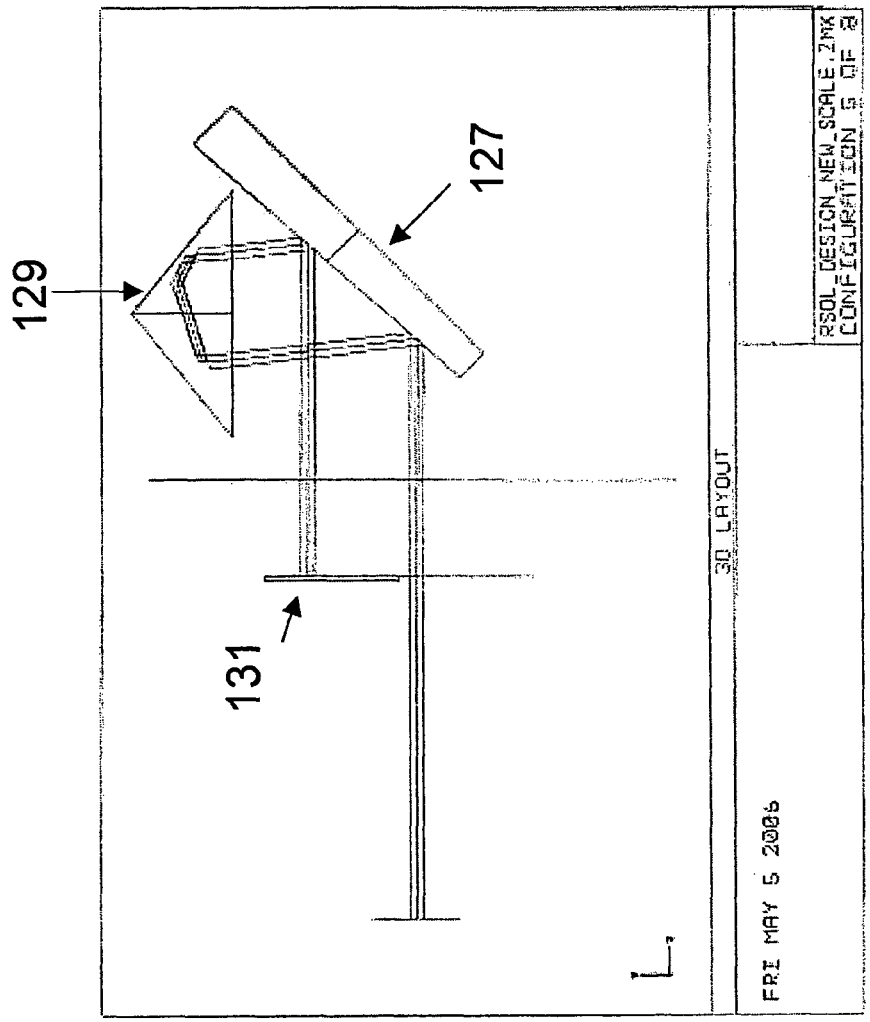

FIG. 17 shows the same view as FIG. 17 however in FIG. 17, the rotational position of the wedged mirror 127 is such that the gap between the mirror 127 and the retro reflector 129 is at its minimum.

Figure 18:
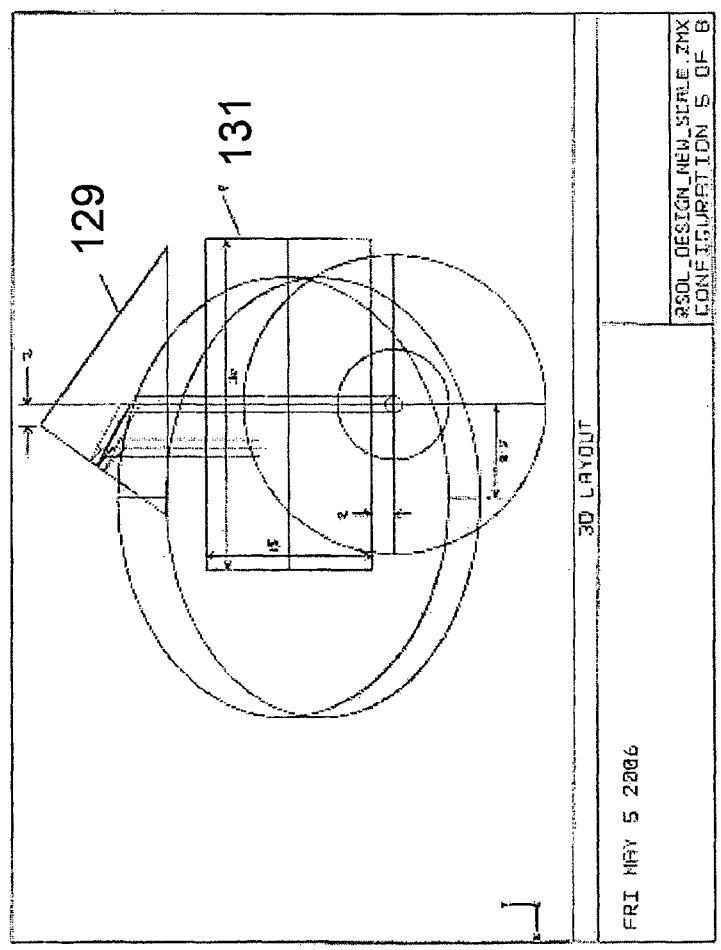

FIG. 18 shows the RSDL 109 viewed from the front, and FIG. 18 shows the view from the top.

In use, the THz system scans both the delay line 109 and the Risley prism pair 11 concurrently. Typically, the scan rate of the delay line 109 is 1 kHz, i.e. 1000 scans per second, the Risley prism pair 11 scans at 67 Hz, while optical pulses are produced by the laser 95 at 80 MHz.

As noted above in relation to FIG. 4, the electrical field at the receiver 39 is capable of being measured only during the period that the receiver 39 is illuminated by optical radiation from the laser 95. Since this period is considerably shorter than the duration of a THz pulse, each optical pulse effectively gives the opportunity to sample the electric field at the receiver 39 for an instantaneous point during the THz pulse. By varying the relative delay imposed between the optical pulses directed to the receiver 17 and transmitter 15 cartridges, the position of the sampling point within the THz pulses can also be varied.

Rather than measuring the electric field at all points during a single reflected THz pulse, the system therefore builds up the electric field profile over a series of THz pulses as the delay line 109 gradually alters the measurement point within the THz pulses. Clearly, this method relies on pulses within the THz pulse train being all being substantially similar so that an accurate profile can be determined.

A reconstructed electric field profile, which equates to a set of measurements of the electrical field of the reflected THz radiation that is collected during one scan of the delay line 109, is hereinafter referred to as a pulse.

During one scan of the delay line, approximately 80,000 measurements of the electrical field are possible. In practice, data need not be recorded from all of these measurements, and a pulse of data generated by the system will generally comprise electrical field measurements from a sub-set of the 80,000 measurements that are possible during one scan of the optical delay line 109. Since each measurement during a scan represents an electrical field measurement made at a different time after the THz pulse was incident on the sample, the time from the start of a pulse will correspond to measurement of the THz radiation field reflected from different depths within the sample under test.

Thus, the scanning produced by the delay line 109 allows analysis of the sample at different depths. The lateral scanning by the Risley prism pair 11 of the focal position of the THz radiation allows measurements to be taken from different points across the sample. The combination of the two types of scan allows a 2-dimensional THz reflectance image of the sample under test to be generated.

Since the delay line 109 scans at a much faster rate than the Risley prisms 11, the motion of the THz focus across the sample during the time taken to complete the delay line scan is sufficiently small that it is ignored for the purposes of these calculations.

Image data in the form of pixels can be derived from the pulses, or from some parameter of the pulses. In particular, image data can be derived by comparing parameters from different pulses.

The pulses are not continuous functions, since they are reconstructed from a collection of measurement points. Pulses may therefore be formed from varying numbers of measurements of the electric field. In addition, the measurements from two different pulses may not have consistent start times relative to the optical pulse, and measurements may even be made at different rates in different pulses.

Figure 19:
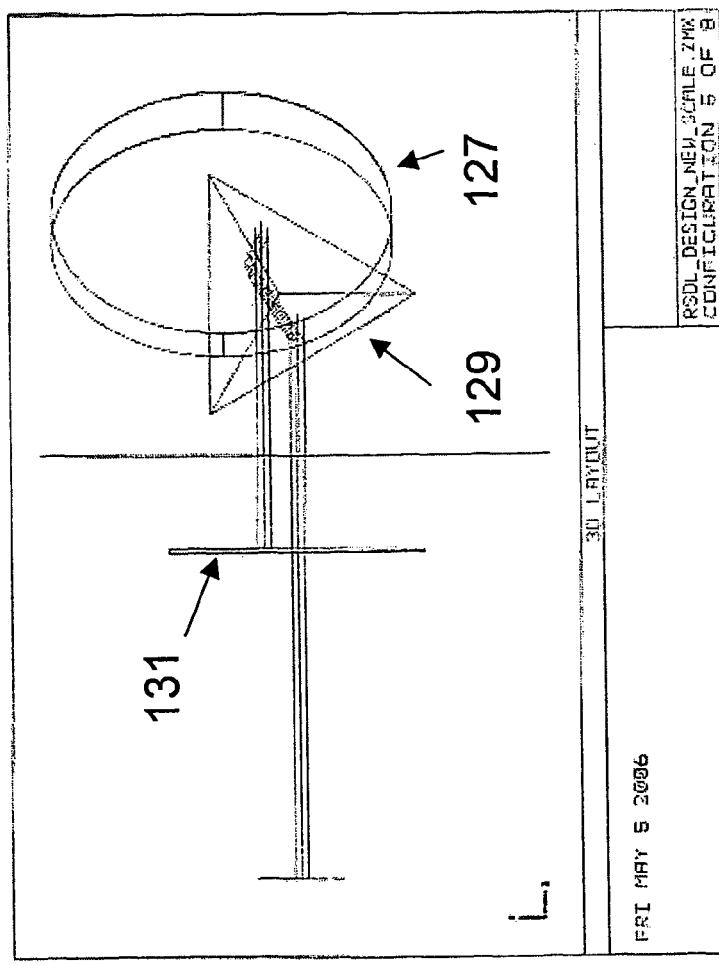
Figure 20:
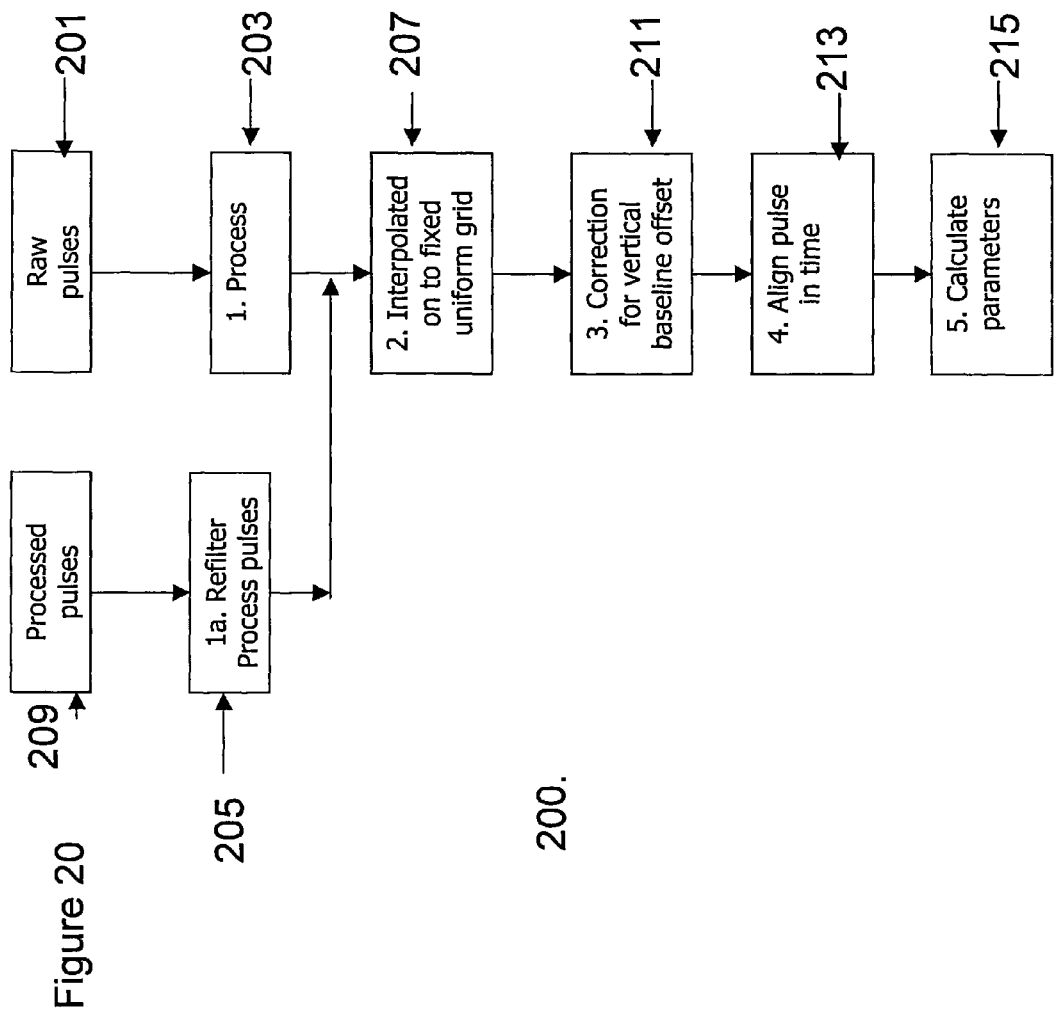
FIG. 20 shows a flow chart of the method of processing data used in the system.

Therefore, pulse data must be processed before it can be used to form images to aid in the determination of the presence or absence of cancerous tissue. FIG. 19 shows a generalised flow chart of the method of processing pulses.

Raw, unprocessed, pulses are input to the processing system 200, these are then processed 203. Alternatively, if processed pulses 209 are input to the processing system, then these are refiltered 205. After either processing or refiltering, the pulses are interpolated onto a fixed grid 207, corrected for any vertical offset in the baseline 211 and aligned in time 213. After the alignment in time 213, parameters may be calculated from the pulses 215.

The above processing steps are described in greater detail below.

In step 201, raw pulses are input to the processing system. The raw pulses are then processed in step 203.

The raw pulse processing of step 203 can be represented mathematically as follows:

$$\text{Pulse} = FFT^{-1}\left[\frac{FFT(\text{signal} - \text{baseline})}{FFT(\text{ref} - \text{baseline})} \times FFT(\text{filter})\right]$$

The processed pulse is the raw data that has had the quartz-baseline subtracted, has been divided by a reference (this calculation is done in the frequency domain) and is filtered by a double Gaussian filter.

References can be obtained by recording a pulse or pulses whilst the probe 1 is not applied to a sample. The reference can be taken while the probe is in contact with, for example, air or water or another material. References may also be taken whilst the probe is applied to a sample of known properties. The examination of certain samples may benefit from more than one reference. For example, when examining tissue from the gastrointestinal tract the applicants note that additional information may be obtained by referencing the tissue under test to both air and water. The applicants also note that the optimum material for obtaining the reference or references may be dependent on the particular sample material under test, or the prevailing conditions under which the sample is tested. Typically, the most suitable reference will be obtained from a material that has properties the closely match the sample material under test.

References are usually obtained immediately before or after the examination of the sample, since this will tend to minimise the effect of any change in the instrument parameters over time. However, references may be taken at other times and stored for later use.

The filter function is in the form of a double Gaussian:

$$f(t) = \frac{1}{u}\exp\left(-\left(\frac{t}{u}\right)^2\right) - \frac{1}{l}\exp\left(-\left(\frac{t}{l}\right)^2\right)$$

where t is time and u and l are upper (High) and lower (Low) bandwidth time constants respectively. The standard high frequency index setting for the filter is 16, and for the low frequency it is 2048. This is for a time step of 0.06563 ps. If the time step is different to this then the high frequency index is inversely scaled as $$\text{scaled High} = (\text{standard time step}/\text{time step}) * \text{standard High}$$

$$= (0.06563/\text{time step}) * 16$$

In step 205, processed pulses are refiltered. The refiltering is necessary to ensure that the pulses are all filtered in the same manner. This is necessary only if the saved data is already processed. The settings for the filter are the standard High and Low frequency filter indices, 16 and 2048 respectively, again inversely scaled to the pulse time domain range $$\text{scaled High} = (\text{standard time step}/\text{time step}) * \text{standard High}$$

$$= (0.06563/\text{time step}) * 16$$

The formula for refiltering is:

Refiltered data=$Re\{FFT^{-1}[FFT(\text{scaled std filter})*FFT(\text{processed})/FFT(\text{filter})]\}$ In step 207 the pulse data are interpolated onto a uniform grid for parameter calculation. This is a time domain range of 512 points, with a time step of 0.06563 ps, starting from 0 ps at the beginning of the pulse.

Step 211 removes any vertical offset in the pulses, so that the starting portion of the pulse is level with the x-axis. This offset is different to the quartz-baseline correction. The baseline shift is implemented by averaging the first 100 points of all the values of the pulse from the start point up to and including 6.4974 ps and subtracting this from the amplitude at all points on the pulse. The significance of 6.4974 ps is that this corresponds to the time of the $100^{th}$ point as 99*0.06563=6.4974.

The equation for each time point is given by:

$\text{Amp}BL(t) = \text{Amp}(t) - \text{mean}(\text{points up to } t = 6.4974 \text{ ps})$ Subsequently, the pulses are aligned in time, since the real and imaginary components of the Fourier transform are affected by the position of the pulse in the time domain. For consistency, all pulses are aligned to the midpoint of the time domain, the $256^{th}$ point which occurs at 16.73565 ps. The value aligned to the $256^{th}$ point is the larger absolute value of either the minimum or maximum, depending on whether the pulse in question is a positively or negatively valued pulse. The points of the pulse are circularly shifted so that the minimum or maximum is moved to the location at $256^{th}$ point. This location is then defined to be the origin, i.e. 0 ps.

Once the above processing has been completed, parameters can be calculated from the processed pulses.

The parameters calculated may include, but are not limited to, the following:

The full width at half maximum of a pulse, the pulse width prior to the maximum or minimum of the pulse, part or all of the integral of the pulse or the integral of the positive or negative values of the pulse and the pulse amplitude at certain times relative to the maximum or minimum value of the pulse.

Parameters may also be calculated from the frequency spectrum of the pulse. The frequency spectrum can for example be determined by performing a fast Fourier transform (FFT) on the time domain pulse. Examples of frequency domain parameters include, but are not limited to:

The power spectrum at certain frequencies, the real or imaginary part of the FFT at certain frequencies or the gradient of the Logarithm of the power spectrum between certain frequency limits.

The applicants have noted that the following specific parameters of THz pulses are of particular relevance when distinguishing between cancerous and healthy breast tissue:

The full width at half maximum of a THz pulse.

The half width of a THz pulse prior to the minimum point, and measured at 30% of the minimum.

The integral of an entire pulse.

The integral of the negative values within a pulse.

The integral of a pulse between the times of −0.5907 ps until 0.3282 ps.

The amplitude of a pulse at a time of 0.5907 ps after the minimum point of the pulse.

The amplitude of a pulse at a time of 0.2625 ps after the minimum point.

The power in the spectrum of a pulse at a frequency of 0.1190 THz.

The real part of the FFT of a pulse at a frequency of 0.1190 THz.

The imaginary part of the FFT of a pulse at a frequency of 0.1488 THz.

The gradient of a linear fit to the logarithm of the power spectrum of a pulse within the frequency range of 0.1190 THz and 1.4582 THz.

As noted above, when examining tissue from the gastrointestinal tract, it may be advantageous to obtain two references. Accordingly, the applicants have also noted that the following specific parameters of THz pulses are of particular relevance when distinguishing between cancerous and healthy colon tissue when using air as a reference:

The minimum value of the THz pulse ($E_{min}$).

The ratio of the minimum to maximum values of the THz pulse.

The amplitude, normalised by $E_{min}$ ($A(t)/E_{min}$), at a time t=0.33 ps prior to the time at which $E_{min}$ occurs.

The amplitude, normalised by $E_{min}$, at a time t=2 ps after the time at which $E_{min}$ occurs.

The integral of the THz pulse from 0.33 ps before the $E_{min}$ time to 2 ps afterwards.

The power in the spectrum of the THz pulse at a frequency f=0.6 THz.

The integral of the power in the spectrum over a fixed freq range from 0.6 THz to 0.44 THz.

The difference between the maximum and the minimum values in the THz pulse.

When examining tissue from the gastrointestinal tract and using water as a reference, the following parameters of the THz pulses are of particular relevance:

The maximum value of the THz pulse ($E_{max}$).

The time at which $E_{max}$ occurs.

The phase angle at a frequency f=0.35 THz.

The integral of the THz pulse from 0.26 ps before the time at which $E_{max}$ occurs to 0.26 ps afterwards.

The power in the spectrum of the THz pulse at a frequency f=0.6 THz.

The integral of the power in the spectrum of the THz pulse over fixed frequency range from 0.6 THz to 0.44 THz The logarithm of the integral of the power spectrum of the THz pulse.

The amplitude of the THz pulse at a time t=0.26 ps prior to the time at which $E_{max}$ occurs.

Clearly, the exact figures specified in the above description of the pulse processing method only represent examples of suitable parameters, filter properties and time-bases. The skilled reader will understand that different figures may be used, and indeed other methods of data processing may also be used.

The above defined parameters will now be described in greater detail with reference to FIGS. 21 to 30.

Figure 21:
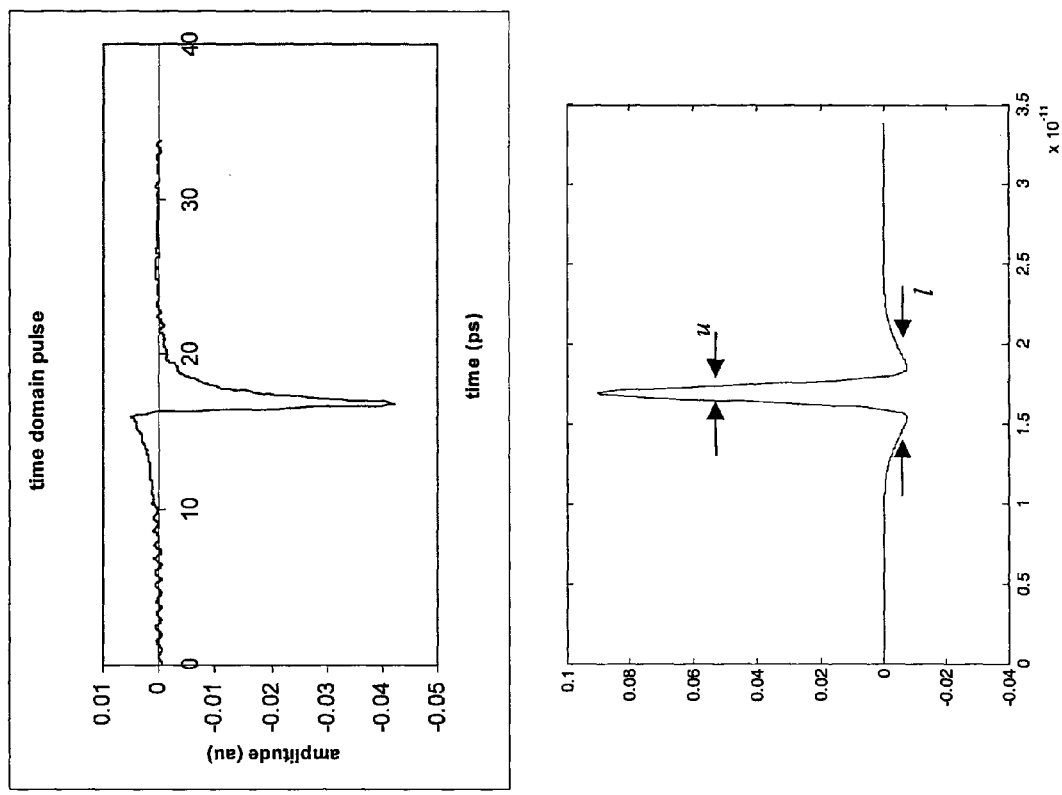
FIGS. 21 to 29 show the calculation of parameters in the system from processed data.

FIG. 21 shows an example of a typical processed pulse, shown in the time domain. The pulse is a negatively valued pulse.

Figure 22:
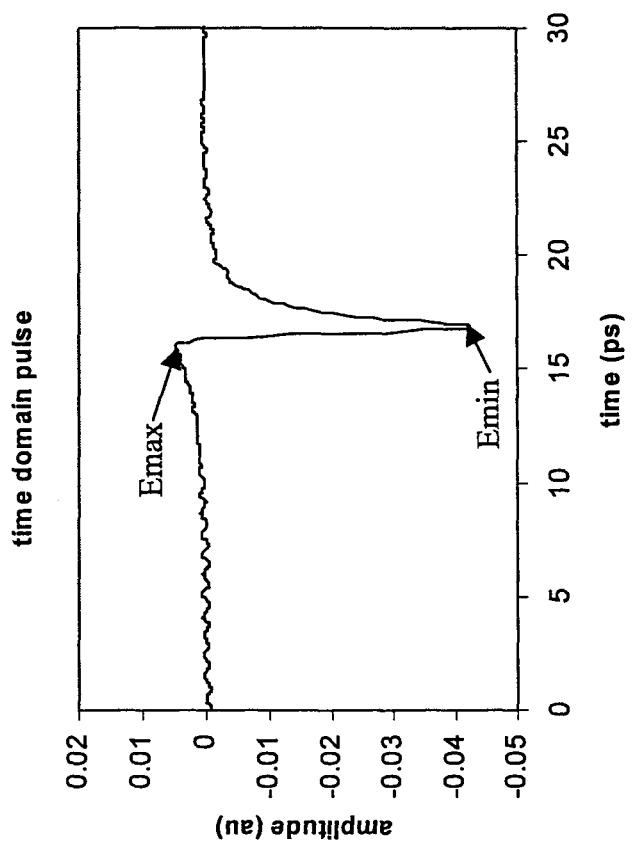

FIG. 22 shows the same pulse with the minimum and maximum values marked, the values, together with the times at which they during the pulse are used in the calculation of certain parameters.

Figure 23:
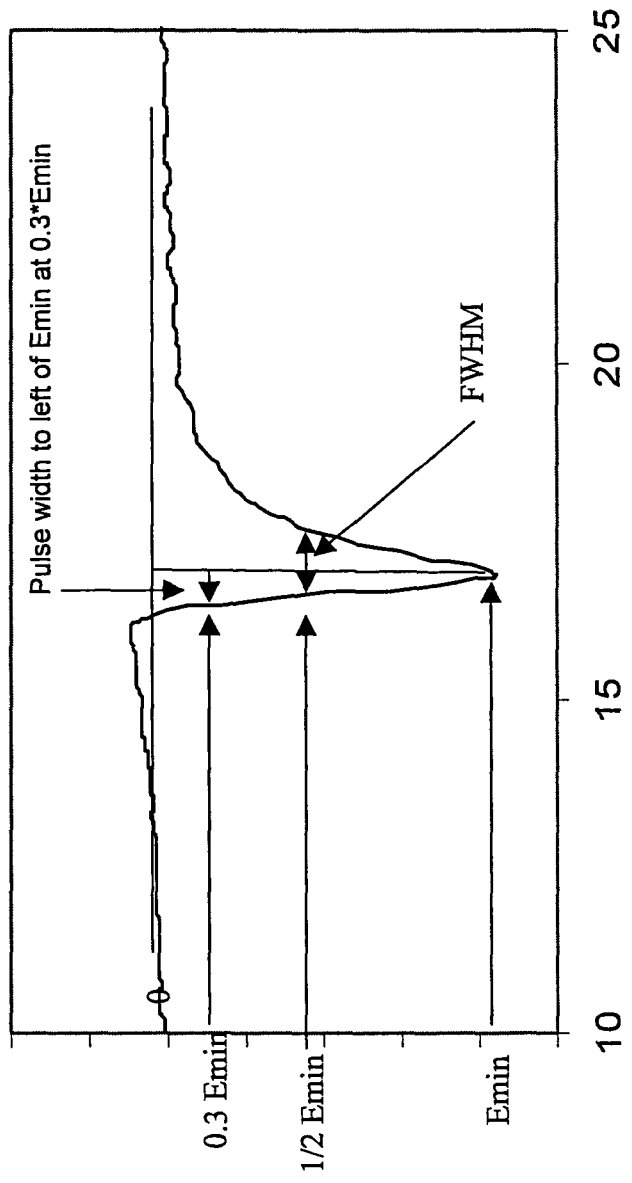

FIG. 23 shows the calculation of the pulse full width half maximum/minimum (FWHM). Since the pulse in question is a negatively valued pulse, the amplitude at the minimum value is first determined, as shown with reference to FIG. 22. The two times at which the pulse amplitude equals half of this value are then determined. The time difference between the two times is then determined, and this the pulse FWHM.

Also shown on FIG. 23 is the calculation of the parameter of the time prior to the minimum amplitude that is 0.3 of the minimum amplitude. Here, the time of the minimum amplitude is first determined. Subsequently, the time prior to the minimum amplitude at which the amplitude is 0.3 of the minimum amplitude is also determined. The time difference between these two times is then defined to be the above parameter.

Figure 24:
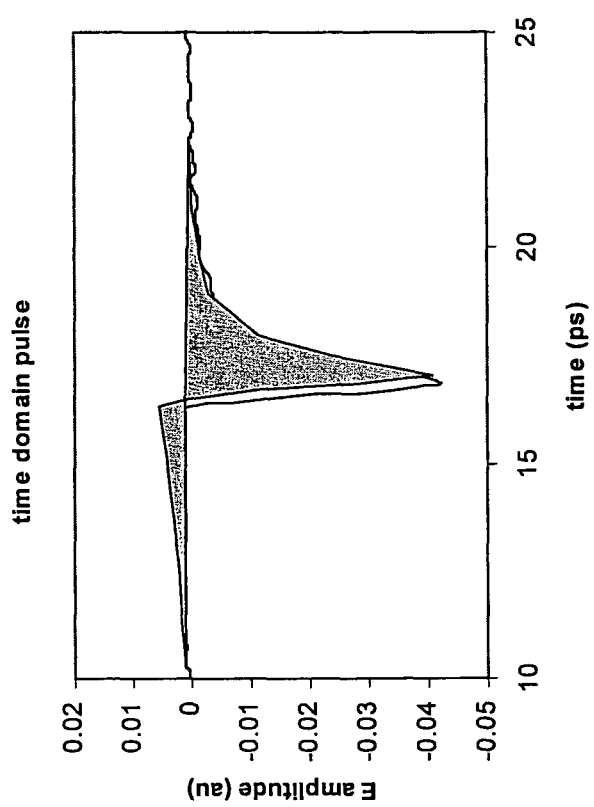

FIG. 24 shows the calculation of the parameter that is the integral of the whole pulse. To calculate this, the sum of all the amplitudes is made over all points in the pulse. For the purpose of calculating this parameter, all amplitudes contribute to the integral, in other words negative amplitudes do not subtract from positive amplitudes.

Figure 25:
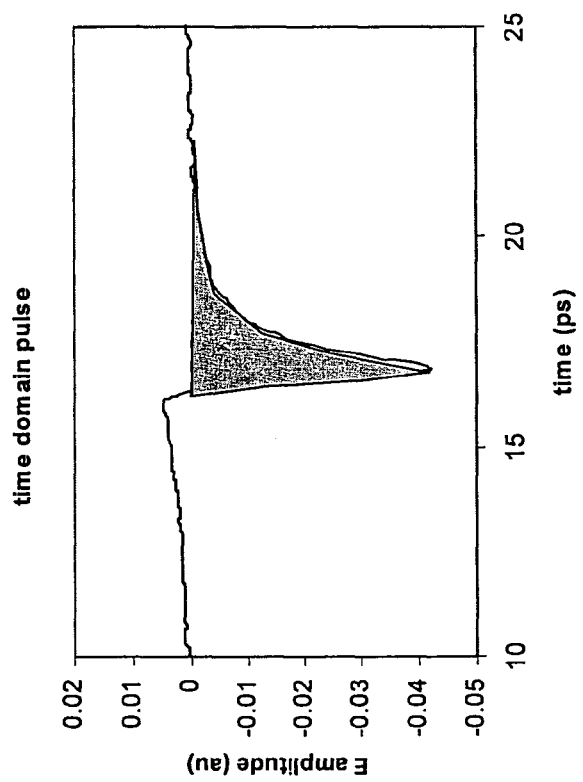

FIG. 25 shows the calculation of the parameter that is the integral of the negative parts of the pulse. To calculate this parameter, only values of the amplitude that are negative in value are considered to contribute to the integral. Thus, the integral is not made over the whole time period of the pulse.

Figure 26:
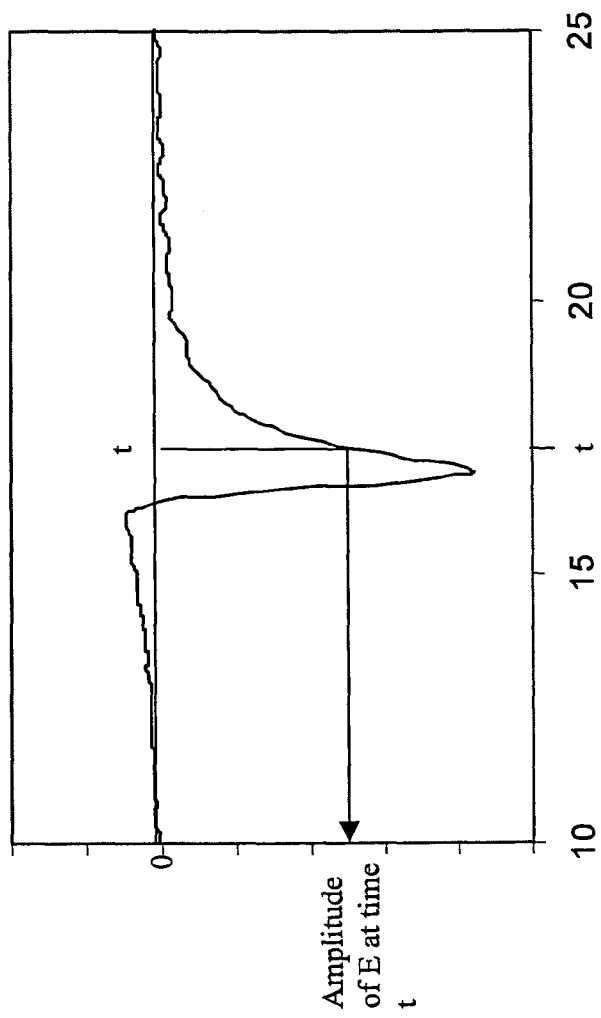

FIG. 26 shows the calculation of parameters that are simply the amplitude of the pulse at a given time.

Figure 27:
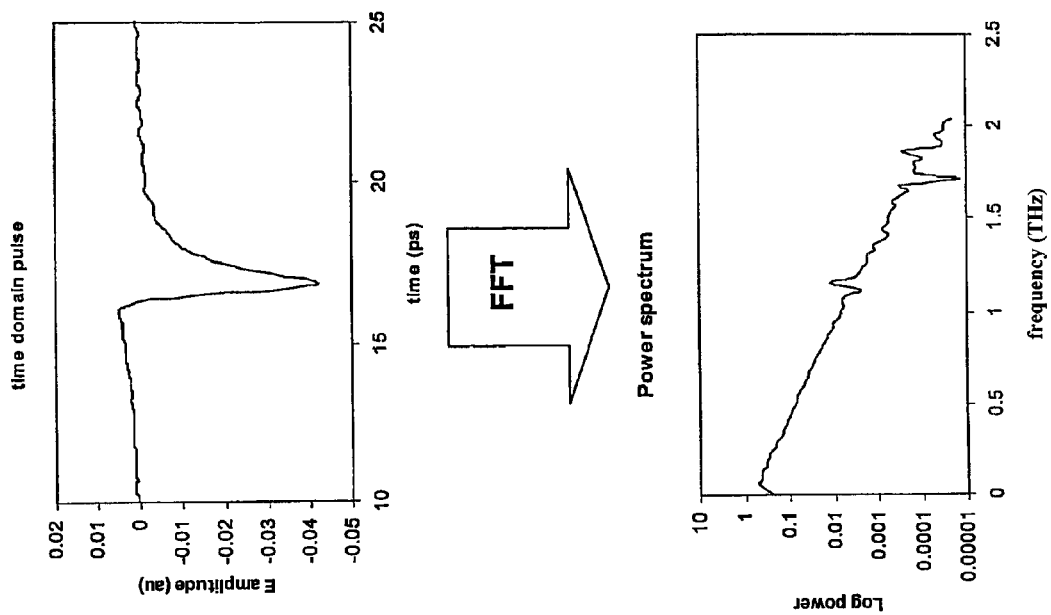
Figure 28:
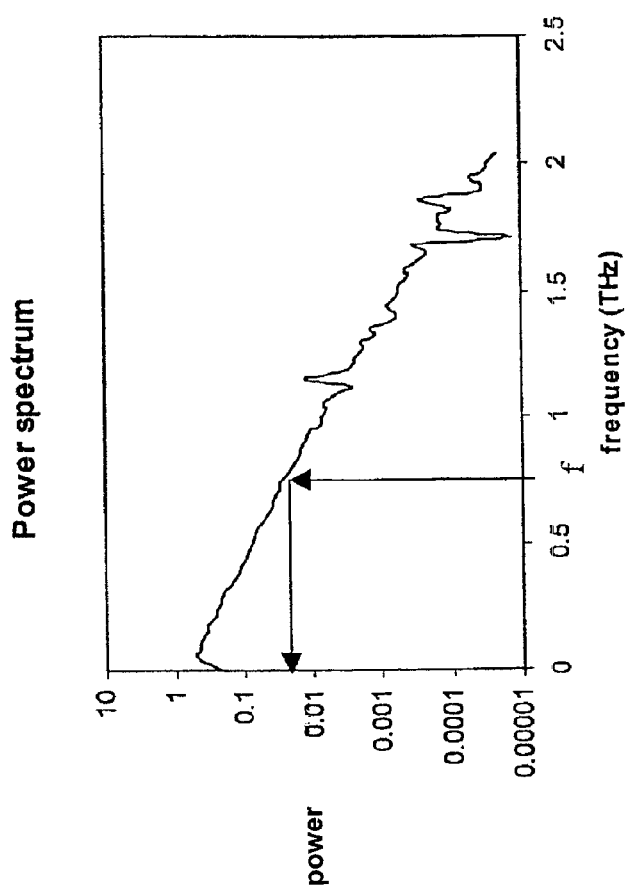
Figure 29:
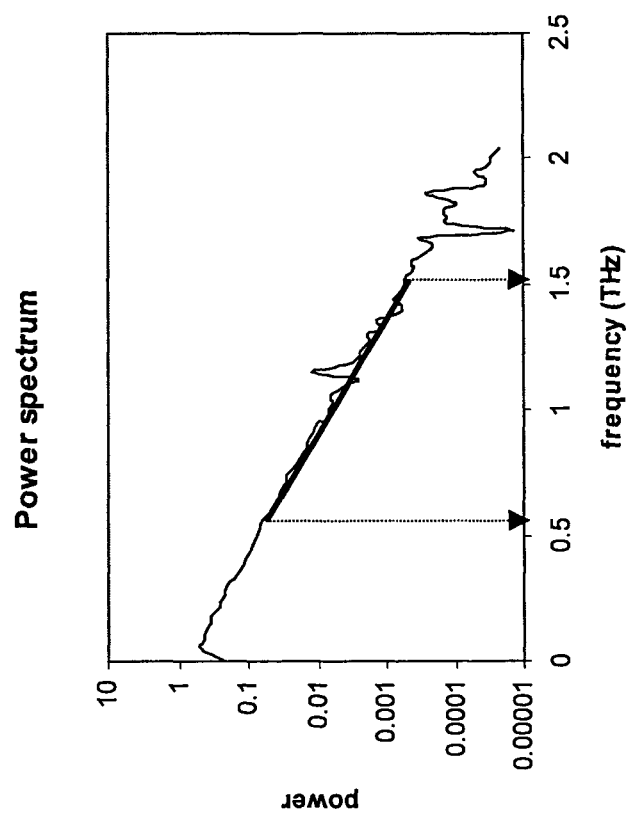

FIGS. 27 to 29 show the calculation of parameters that are in the frequency domain. As shown in FIG. 27, to calculate such parameters, a pulse in the time domain must first be converted into the frequency domain by means of a Fast Fourier Transform (FFT). Multiplying the FFT by its complex conjugate and dividing the result by the number of time points in the pulse will then yield a power spectrum. FIG. 27 also shows such a power spectrum.

From the power spectrum in FIG. 27, parameters such as that shown in FIG. 28 can be derived. In FIG. 28, the power in the spectrum at a given frequency has been determined.

In FIG. 29, a linear fit to the power spectrum has been made in a given frequency range. The gradient of this linear fit is then measured.

The invention claimed is:

1. A THz radiation probe for examining an object, the probe comprising a first portion configured to be inserted into an opening of said object in a first direction, said probe further comprising
   at least one THz emitter,
   a directing unit for directing THz radiation emitted from said emitter to said object via an aperture located at said first portion and subsequently from said object to at least one THz detector and,
   a scanning unit for scanning said emitted THz radiation across said object in a scan direction, said scan direction having a component in said first direction,
   wherein the directing unit comprises an elongate solid dielectric member, the elongate direction of the elongate solid member being parallel to the first direction, the elongate solid dielectric member comprising a plane surface reflective to THz radiation angled to the first direction, the refractive index of the solid dielectric member and the plane surface being configured such that THz radiation emitted by the emitter undergoes reflection at the plane surface and is directed towards the aperture, the scanning of the THz beam across the plane surface causing the scanning of the THz beam across the aperture.

2. A THz radiation probe according to claim 1, wherein a part of said THz radiation probe comprising said first portion or a part thereof is configured to be detachable.

3. A THz radiation probe according to claim 1, wherein THz radiation that is reflected from said object is directed by said directing unit to said THz detector.

4. A THz radiation probe according to claim 1 wherein said emitted THz radiation is focused at said aperture.

5. A THz radiation probe according to claim 1 wherein said scanning unit comprises a pair of Risley prisms.

6. A THz probe according to claim 1 wherein said THz emitters are photoconductive antennas that comprise at least one dipole antenna having a resonant frequency in the THz frequency regime.

7. A THz radiation probe according to claim 1, wherein said planar surface is oriented such that the normal to said surface is at an angle of approximately 45° to said first direction.

8. A THz radiation probe according to claim 1 further comprising a sheath that substantially encloses said first portion.

9. A THz radiation probe according to claim 8, wherein said sheath comprises a material that is substantially transmissive to THz radiation.

10. A THz radiation probe according to claim 8, wherein said sheath comprises a region of material that is substantially transmissive to THz radiation, that is located adjacent to said aperture such that THz radiation may pass through said region.

11. A THz radiation probe according to claim 8, wherein said sheath or a part thereof is disposable.

12. A THz radiation probe according to claim 1, wherein THz radiation is emitted from said THz emitter is pulsed radiation.

13. A THz radiation probe according to claim 12, further comprising a time resolved detection unit.

14. A THz probe according to claim 13, wherein said time resolved detection unit comprises an optical delay line.

15. A THz probe according to claim 14, wherein said optical delay line comprises a mirror that rotates about an axis that is not collinear with the normal to said mirror's reflective surface.

16. A method of examining a surgical opening comprising
inserting a first portion of a probe into said surgical opening in a first direction,
directing THz radiation emitted from at least one emitter through an elongate solid dielectric member, the elongate direction of the elongate solid member being parallel to the first direction, the elongate solid dielectric member comprising a plane surface reflective to THz radiation angled to the first direction, the refractive index of the solid dielectric member and the plane surface being configured such that THz radiation emitted by the emitter undergoes reflection at the plane surface and is directed towards the sidewall of said opening via an aperture in said first portion,
directing THz radiation returned from said sidewall to at least one THz detector and,
scanning said emitted THz radiation across said sidewall in said first direction by scanning of the THz beam across the plane surface.

17. A method of analyzing an object comprising
inserting a first portion of a probe into an opening in a first direction,
directing THz radiation emitted from at least one emitter through an elongate solid dielectric member, the elongate direction of the elongate solid member being parallel to the first direction, the elongate solid dielectric member comprising a plane surface reflective to THz radiation angled to the first direction, the refractive index of the solid dielectric member and the plane surface being configured such that THz radiation emitted by the emitter undergoes reflection at the plane surface and is directed towards said object via an aperture in said first portion,
directing THz radiation returned from said object to at least one THz detector and,
scanning said emitted THz radiation across said object in said first direction by scanning of the THz beam across the plane surface.

18. A method according to claim 16, wherein THz radiation that is reflected from said object is collected and directed to said THz detector.

19. A method according to claim 16, wherein said position scanning is achieved using a pair of Risley prisms.

20. A method according to claim 16, wherein THz radiation obtained at different times is used in producing measurements from different depths in said object.

21. A method according to claim 16, wherein THz radiation received at said THz detector is sampled in time.

22. A method according to claim 21, wherein the sampling rate is greater than the rate at which the THz radiation is scanned in said first direction.

23. A method according to claim 21, wherein the sampling rate is substantially greater than the scanning rate.

24. A method according to claim 16, wherein said scanning is continuous.

25. A method according to claim 16, wherein THz radiation received at said THz detector is compared with THz radiation received whilst said probe was arranged to detect THz radiation from a known sample or samples.

26. A method according to claim 25 wherein said known sample or samples are either water or air or both.

27. A method according to claim 16, wherein a parameter or parameters of said returned THz radiation is measured and subsequently presented.

* * * * *